US006348569B1

(12) United States Patent
Walker et al.

(10) Patent No.: US 6,348,569 B1
(45) Date of Patent: Feb. 19, 2002

(54) SPRUCE BUDWORM ANTIFREEZE PROTEINS, GENES AND METHOD OF USING SAME

(75) Inventors: Virginia K. Walker, Sydenham; Peter L. Davies, Kingston; Mitra Rahavard, Kingston; Michael G. Tyshenko, Kingston, all of (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 09/434,323

(22) Filed: Nov. 4, 1999

Related U.S. Application Data

(60) Division of application No. 08/868,594, filed on Jun. 3, 1997, now Pat. No. 6,008,016, which is a continuation-in-part of application No. 08/657,264, filed on Jun. 3, 1996, now abandoned.

(51) Int. Cl.[7] .................................................. C07K 14/00
(52) U.S. Cl. ..................................... 530/300; 530/350
(58) Field of Search ................................ 530/350, 300; 435/69.1

(56) References Cited

U.S. PATENT DOCUMENTS

| | | | |
|---|---|---|---|
| 5,118,792 A | 6/1992 | Warren et al. | 530/350 |
| 5,296,462 A | 3/1994 | Thomashow | 514/2 |
| 5,356,816 A | 10/1994 | Thomashow | 435/320.1 |
| 5,358,931 A | 10/1994 | Rubinsky et al. | 514/12 |
| 5,627,051 A | 5/1997 | Duman | 435/69.1 |
| 5,633,451 A | 5/1997 | Duman | 800/205 |

OTHER PUBLICATIONS

Chakrabartty, A., and Hew, C.L., "The effect of enhanced α-helicity on the activity of a winter flounder antifreeze polypeptide", *Eur. J. Biochem.* 202: 1057–1063 (1991).

Davies, P.L., and Hew, C.L., "Biochemistry of fish antifreeze proteins", *FASEB J.* 4: 2460–2468 (1990).

DeVries, "Antifreeze Peptides and Glycopeptides in Cold-Water Fishes", *Annu. Rev. Physiol.* 45:245–260 (1983).

Duman, J., and Horwath, K., "The role of hemolymph proteins in the cold tolerance of insects", *Ann. Rev. Physiol.* 45: 261–270 (1983).

Fourney, R.M., Joshi, S.B., Kao, M.H., and Hew, C.L., "Heterogeneity of antifreeze polypepetides from the Newfoundland winter flounder, Pseudopleuronectes americanus", *Can. J. Zool.* 62: 28–33 (1984).

Griffith M. and Ewart, K. Vanya, "Antifreeze Proteins and Their Potential use in Frozen Foods", *Biotechnology Advances*, vol. 13, No. 3, pp 375–402 (1995).

Hayes P.H. et al., "Crystalline–Rich Type II Antifreeze Protein Precursor is initiated from the Third AUG Codon of its mRNA," *The Journal of Biological Chemistry*, vol. 264, No. 31, Nov. 5, pp. 18761–18767 (1989).

Hew, C.L., Kao, M.H., So, Y.-P., and Lim, K.-P., "Presence of cystine–containing antifreeze proteins in the spruce budworm, Choristoneura fumiferana", *Can. J. Zool.* 61: 2324–2328 (1983).

Lawson, "Poliovirus thiol proteinase 3C can utilize a serine nucleophile within the putative catalytic triad", *Proc. Natl. Acad. Sci.*, 88:9919–9923 (1991).

Li, X.–M., Trinh, K.–Y., Hew, C.L., Buettner, B., Baenziger, J., and Davies, P.L., "Structure of an antifreeze polypeptide and its precursor from the ocean pout, Macrozoarces americanus", *J. Biol. Chem.* 260: 12904–12909.

Ng, N. F., Trinh, K. Y., and Hew, C.L., "Structure of an antifreeze polypeptide precursor from the sea raven, Hemitripterus americanus", *J. Biol. Chem.* 261: 15690–15695 (1986).

Ochman, H., Gerber, A.S., and Hartl, D.L., "Genetic applications of an inverse polymerase chain reaction", *Genetics* 120: 621–623 (1988).

Patterson & Duman, "Composition of a Protein Antifreeze from Larvae of the Beetle", *J. Exp. Zool.* 210:361–367 (1979).

Rubin, G.M., and Spradling, A.C., "Vectors for P element–mediated gene transfer in Drosophila", *Nucl. Acids Res.* 11: 6341–6351 (1983).

Rubin, G.M., and Spradling, A.C., "Genetic transformation of Drosophila with transposable element vectors", *Science* 218: 348–353 (1982).

Saiki, R.K., Scharf, S., Faloona, F., Mullis, K.B., Horn, G.T., Erlich, H.A., and Arnheim, N., "Enzymatic amplification of β–globin genomic sequences and restriction.site analysis for diagnosis of sickle cell anemia", *Science* 230: 1350–1354 (1985).

Slaughter, D. et al. Antifreeze proteins from the sea raven, Hemitripterus americanus , *J. Biol. Chem* 256: 2022–2026 (1981).

Tang, W., and Baust, J., "Studies of structure–function relationship of insect antifreeze proteins", Poster & Abstract, American Society for Biochemistry and Molecular Biology (ASBMB) Conference, Washington, D.C., (May 21–25, 1994).

Tomchaney, A.P., Morris, J.P., Kang, S.H., and Duman, J.G., "Purification, composition, and physical properties of a thermal hysteresis 'antifreeze' protein from larvae of the beetle, Tenebrio molitor", *Biochem.* 21: 716–721 (1982).

Wu, et al., Purification and characterization of antifreeze proteins from larvae of the beetle Dendroides canadensis, *J. Comp. Physiol. B* 161:271–278 (1991).

Yin Weh and Feeney R.E., "Antifreeze Proteins: Structures and Mechanisms of Function" *Chemical Reviews*, vol. 96, No. 2, pp. 601–617 (1996).

*Primary Examiner*—Nashaat T. Nashed
(74) *Attorney, Agent, or Firm*—Townsend and Townsend and Crew LLP

(57) ABSTRACT

A novel class of thermal hysteresis, antifreeze proteins (THPs) has been isolated and purified from Choristoneura sp., including the eastern spruce budworm C. fumiferana. The invention provides for nucleic acids which encode these antifreeze proteins. The invention also provides for antibodies reactive to these novel antifreeze proteins. The invention also includes a method for decreasing the freezing point of an aqueous solution by adding these novel antifreeze proteins to the solution.

14 Claims, 3 Drawing Sheets

```
M   K   C   L   M   L   I   M   A   L   A   I   I   N   T   V   S   S   D   G
ATG AAG TGT TTA ATG CTG ATC ATG GCT CTA GCC ATT ATC AAC ACT GTA TCT TCT GAT GGC

S   C   T   N   T   N   S   Q   L   S   A   N   S   K   C   E   K   S   T   L
TCG TGT ACA AAC ACG AAC TCT CAG CTC AGC GCA AAC TCC AAG TGC GAA AAA TCG ACG TTG

T   N   C   Y   V   D   K   S   E   V   Y   G   T   T   C   T   G   S   R   F
ACC AAC TGC TAC GTC GAT AAA AGC GAG GTT TAC GGC ACT ACC TGT ACA GGA AGC CGA TTC

D   G   V   T   I   T   T   S   T   G   S   R   I   S   G   P   G   C
GAC GGG AGT CAC TAT AAC GAC TTC AAC ATC TAC CGG TTC ACG TAT TCA GGC CCT GGA TGC

K   I   S   T   C   I   I   T   G   G   V   P   A   P   S   A   A   C   K   I
AAG ATT TCC ACT TGC ATT ATC ACC GGG GGT GTA CCT GCT CCA TCA GCT GCT TGC AAG ATT

S   G   C   T   F   S   A   N   Ter                    (SEQ ID NO:2)
TCT GGA TGT ACT TTC AGT GCT AAT TAA           (nuc. 65-391 OF SEQ ID NO:1)
```

FIG. 2

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 1387 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 65..391
      (D) OTHER INFORMATION: /product= "THP precursor"
          /note= "spruce budworm (Choristoneura
          sp.) thermal hysteresis protein (THP)
          precursor"

(xi) SEQUENCE DESCRIPTION: SEQ ID NO:1:

```
CGGCACGAGG AAAGACATAT TTTTTTTTTA GTTTCAAAAG TTGTGTACAT TTTTCTCAAG        60

TATC ATG AAG TGT TTA ATG CTG ATC ATG GCT CTA GCC ATT ATC AAC ACT       109
     Met Lys Cys Leu Met Leu Ile Met Ala Leu Ala Ile Ile Asn Thr
      1               5                  10                  15

GTA TCT TCT GAT GGC TCG TGT ACA AAC ACG AAC TCT CAG CTC AGC GCA         157
Val Ser Ser Asp Gly Ser Cys Thr Asn Thr Asn Ser Gln Leu Ser Ala
                 20                  25                  30

AAC TCC AAG TGC GAA AAA TCG ACG TTG ACC AAC TGC TAC GTC GAT AAA         205
Asn Ser Lys Cys Glu Lys Ser Thr Leu Thr Asn Cys Tyr Val Asp Lys
             35                  40                  45

AGC GAG GTT TAC GGC ACT ACC TGT ACA GGA AGC CGA TTC GAC GGA GTC         253
Ser Glu Val Tyr Gly Thr Thr Cys Thr Gly Ser Arg Phe Asp Gly Val
         50                  55                  60

ACT ATA ACG ACT TCA ACA TCT ACC GGT TCA CGT ATT TCA GGC CCT GGA         301
Thr Ile Thr Thr Ser Thr Ser Thr Gly Ser Arg Ile Ser Gly Pro Gly
     65                  70                  75

TGC AAG ATT TCC ACT TGC ATT ATC ACC GGG GGT GTA CCT GCT CCA TCA         349
Cys Lys Ile Ser Thr Cys Ile Ile Thr Gly Gly Val Pro Ala Pro Ser
 80                  85                  90                  95
```

```
GCT GCT TGC AAG ATT TCT GGA TGT ACT TTC AGT GCT AAT TAAGCCATGA    398
Ala Ala Cys Lys Ile Ser Gly Cys Thr Phe Ser Ala Asn
                100                 105

AAGTCGTCCG AGATTGAGTT TGGCCATTTC ATATGTAAGT AGAATAGGCT AGTGGCTTAA    458

AAAATGTAAT GAGTCCCGTC AGTTAGAATA TCAAAAAACA TGTATTTTTT CGGTTACCTA    518

TATAATGATT CGCCGACAAT TCTTACGCAG ATTATTGATT GGCAGACAAC GTTTCGCCGA    578

GTAAAGGTAC GCTGATGAAT TGAGCGCAT ATGTATTGTT TCGCGTACTA ACGTTTAATT     638

GACTATTTAT TCATTCAGTT GGCTTATGGG TCAGTAAGCC GAGCAACTAA TAACAGAAAT    698

TCGTTTAGCC GATTAATCAC TACACATTTT GAACGTTTAC TCAAACAAGT TTTCGCTTTA    758

GAATTTGTGA TTATTTTAAA TTTAAAGTCA AAACAAACCA CGTCGCGACA CGCCAGCAGT    818

TCGGTTATTG TTTGCCGCAA TTCTACCTAA CACTCCTCCT CGCTGACGCT CGTCGTTGCA    878

CCTAACTATA TTTCGGTGCC ATGTGATAAC TCTGCTTATC ATGTTCCGGC GAACAGTTGT    938

TCGCTTAACT CAAACAATTA CGAACCAAAC AATCGAATAA ACGTAAATCT GCATACCGCA    998

ATTCTTTCGT ACCGACTACT CGGCGAAATG AATAATAGGC GTAACAATAT TATACCAAAC   1058

GTTGCTCGGC AAAAGAAAA ATCTGCGTAA TCAAACTCGG CGAATCGACC GGTCACCATT    1118

ATCACTGAAA TAGATGGCCG TAAATTGTAA TCTATTAATT TAATCGATTA ACATGTTTAT   1178

AATAGAATAA TAAATATTAC TTAACATTAC TTAGTATTAA ATGATAGTAA CATATTTTAA   1238

CACTAGAGGG CTAGAAAATT AAAATAAAGC TTACATTATG CTACTCTAAT GACGGACTAA   1298

AAAGATTTTT TTTCCCCAAT TACCACTGTA CTTACTGTTT TTAAATATTT TAAAATACAG   1358

AAATTGTAAC CAAAAAAAAA AAAAAAAA                                    1387

(2) INFORMATION FOR SEQ ID NO:2:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Cys Leu Met Leu Ile Met Ala Leu Ala Ile Ile Asn Thr Val
  1               5                  10                  15

Ser Ser Asp Gly Ser Cys Thr Asn Thr Asn Ser Gln Leu Ser Ala Asn
                 20                  25                  30

Ser Lys Cys Glu Lys Ser Thr Leu Thr Asn Cys Tyr Val Asp Lys Ser
             35                  40                  45

Glu Val Tyr Gly Thr Thr Cys Thr Gly Ser Arg Phe Asp Gly Val Thr
         50                  55                  60

Ile Thr Thr Ser Thr Ser Thr Gly Ser Arg Ile Ser Gly Pro Gly Cys
 65                  70                  75                  80

Lys Ile Ser Thr Cys Ile Ile Thr Gly Gly Val Pro Ala Pro Ser Ala
                 85                  90                  95

Ala Cys Lys Ile Ser Gly Cys Thr Phe Ser Ala Asn
                100                 105

(2) INFORMATION FOR SEQ ID NO:3:

(i) SEQUENCE CHARACTERISTICS:
        (A) LENGTH: 90 amino acids
        (B) TYPE: amino acid
        (C) STRANDEDNESS:
        (D) TOPOLOGY: linear
```

```
    (ii) MOLECULE TYPE: protein (ix) FEATURE:
         (A) NAME/KEY: Protein
         (B) LOCATION: 1..90
         (D) OTHER INFORMATION: /note= "mature THP"

(xi) SEQUENCE DESCRIPTION: SEQ ID NO:3:

Asp Gly Ser Cys Thr Asn Thr Asn Ser Gln Leu Ser Ala Asn Ser Lys
1               5                  10                  15

Cys Glu Lys Ser Thr Leu Thr Asn Cys Tyr Val Asp Lys Ser Glu Val
            20                  25                  30

Tyr Gly Thr Thr Cys Thr Gly Ser Arg Phe Asp Gly Val Thr Ile Thr
        35                  40                  45

Thr Ser Thr Ser Thr Gly Ser Arg Ile Ser Gly Pro Gly Cys Lys Ile
    50                  55                  60

Ser Thr Cys Ile Ile Thr Gly Gly Val Pro Ala Pro Ser Ala Ala Cys
65                  70                  75                  80

Lys Ile Ser Gly Cys Thr Phe Ser Ala Asn
                85                  90

(2) INFORMATION FOR SEQ ID NO:4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

CATATGCATA TGGATGGCTC GTGTACAAAC AC                              32

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

AAGCTTAAGC TTTTAATTAG CACTGAAAGT ACA                             33

(2) INFORMATION FOR SEQ ID NO:6:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Phe Asp Gly Val Thr Ile Thr Ser Ser Thr Ser Thr Gly Ser Arg
1               5                  10                  15

(2) INFORMATION FOR SEQ ID NO:7:

(i) SEQUENCE CHARACTERISTICS:
        (A) LENGTH: 22 amino acids
        (B) TYPE: amino acid
```

```
        (C) STRANDEDNESS:
        (D) TOPOLOGY: linear (ii) MOLECULE TYPE: peptide (xi) SEQUENCE DESCRIPTION: SEQ ID NO:7:

Ser Thr Leu Thr Asn Cys Tyr Val Asp Lys Ser Glu Val Tyr Gly Thr
1               5                   10                  15

Thr Cys Thr Gly Ser Arg
            20

(2) INFORMATION FOR SEQ ID NO:8:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Ile Ser Ser Cys Ile Ile Thr Gly Gly Val Pro Ala Pro Ser Ala Ala
1               5                   10                  15

Cys Lys (2) INFORMATION FOR SEQ ID NO:9:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Asp Gly Thr Xaa Thr Asn Thr Asn Ser Gln Leu Ser Ala Asn Ser Gln
1               5                   10                  15

Xaa Asp Lys Ser Thr Leu Thr Asn Xaa
            20                  25

(2) INFORMATION FOR SEQ ID NO:10:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Asp Gly Thr Xaa Arg Asn Thr Asn Ser Gln Ile Thr Asn Ser Gln Gly
1               5                   10                  15

Xaa Asp Arg (2) INFORMATION FOR SEQ ID NO:11:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide
```

(xi) SEQUENCE DESCRIPTION: SEQ ID NO:11:

Met Lys Cys Leu Met Leu Ile Met Ala Leu Ala Ile Ile Asn Thr Val
1               5                   10                  15

Ser Ser (2) INFORMATION FOR SEQ ID NO:12:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = N-acetyl cysteine"

(ix) FEATURE:
        (A) NAME/KEY: Modified-site
        (B) LOCATION: 16
        (D) OTHER INFORMATION: /product= "OTHER"
            /note= "Xaa = valinamide"

(xi) SEQUENCE DESCRIPTION: SEQ ID NO:12:

Xaa Asp Lys Ser Thr Leu Thr Asn Ala Tyr Val Asp Lys Ser Glu Xaa
1               5                   10                  15

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

TGAAGTGTTT AATGCTGATC ATG                                        23

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

CATTAGAGTA GCATAATGTA AGC                                        23

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

TCCAAGTGCG AAAAATCGAC G                                          21

-continued (2) INFORMATION FOR SEQ ID NO:16:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:16:

GCTGATGGAG CAGGTACACC                                               20

(2) INFORMATION FOR SEQ ID NO:17:

(i) SEQUENCE CHARACTERISTICS:
       (A) LENGTH: 327 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: misc_feature
       (B) LOCATION: 1..327
       (D) OTHER INFORMATION: /product= "THP precursor"
           /note= "cDNA coding sequence corresponds
           to positions 65-391 of SEQ ID NO:1 cDNA"

(xi) SEQUENCE DESCRIPTION: SEQ ID NO:17:

ATGAAGTGTT TAATGCTGAT CATGGCTCTA GCCATTATCA ACACTGTATC TTCTGATGGC    60

TCGTGTACAA ACACGAACTC TCAGCTCAGC GCAAACTCCA AGTGCGAAAA ATCGACGTTG   120

ACCAACTGCT ACGTCGATAA AAGCGAGGTT TACGGCACTA CCTGTACAGG AAGCCGATTC   180

GACGGAGTCA CTATAACGAC TTCAACATCT ACCGGTTCAC GTATTTCAGG CCCTGGATGC   240

AAGATTTCCA CTTGCATTAT CACCGGGGGT GTACCTGCTC CATCAGCTGC TTGCAAGATT   300

TCTGGATGTA CTTTCAGTGC TAATTAA                                      327

SPRUCE BUDWORM ANTIFREEZE PROTEINS, GENES AND METHOD OF USING SAME

CROSS REFERENCE TO RELATED APPLICATIONS

This application is a divisional of and claims the benefit of U.S. application Ser. No. 08/868,594, filed Jun. 3, 1997, now U.S. Pat. No. 6,008,016 which is a continuation in part of U.S. application Ser. No. 08/657,264 filed Jun. 3, 1996, now abandoned.

BACKGROUND OF THE INVENTION

In modern times, refrigeration and, particularly, freezing have become common and preferred means for storage of biological materials. While refrigeration preserves some important properties of the samples, others continue to deteriorate at a slow but significant rate. Frozen storage may arrest most of this deterioration, but the combination of freezing and thawing introduces other changes which destroy other important properties.

In the modern world, frozen foods have become a mainstay of the human diet. To ensure a high quality product, sufficient for the demanding consumer's palate, frozen vegetables in particular, and frozen desserts, such as ice cream, have been the subject of extensive research by food processors. It is now known that recrystallization can have a substantial negative impact on the taste and texture of frozen foods. The advent of frost-free freezers has exacerbated this situation, which has been more traditionally associated with temperature fluctuations during transportation. After a relatively short period of time at other than sub-zero temperatures or even at sustained freezing temperatures, many frozen foods become less desirable, or worse, totally unsuitable, for human consumption.

While a variety of techniques have been implemented to mitigate the damages associated with recrystallization, and limited success has been attained, significant problems remain. Often, modifications to the processing of the frozen foods drastically affect their quality, color, flavor, and/or texture. Moreover, the additional processing can be very expensive and time consuming, rendering the techniques uneconomical. Similar difficulties have been associated with incorporating additives to the foodstuffs.

For biologics, such as therapeutic drugs, blood plasma, mammalian cells for use in tissue culture, and the like, freezing can cause extensive damage. For example, the freezing process itself kills most eukaryotic cells, and cells subjected to even one freezing and thawing cycle exhibit greatly reduced viability. Impaired function of living cells is also prevalent in tissue cryopreservation, with concomitant drawbacks for organ transplants. Similarly, frost or other freezing damage to plants presents a serious problem in agriculture. Finally, drugs can become ineffective, or even dangerous, if not maintained under required strict temperature conditions.

Although the first description of protein-mediated thermal hysteresis (TH) was noted in *Tenebrio molitor* approximately 30 years ago (Grimstone, et al., *Philos. Trans.* B 253:343 (1968)), numerous attempts to purify these thermal hysteresis proteins (THP) failed to yield pure fractions with enough TH to account for the hemolymph activity (Grimstone, et al., (1968); Patterson & Duman, *J. Exp. Zool.* 210:361 (1979); Schneppenheim & Theede *Comp. Biochem. Physiol.* 67B:561 (1980); Tomchaney, et al., *Biochemistry* 21:716 (1982); Paterson Duman *J. Exp. Zool.* 219:381 (1982); and (Horwath, et al., *Eur. J. Entomol.* 93: 419 (1996)). Homogeneity of these proteins was not proven, and they differed in amino acid composition from each other and from the compositions reported here.

There exists a need for new techniques and compositions suitable for improving the preservation characteristics of organic materials at low temperatures, including storage of frozen foods and the viability of biologics. Ideally, these techniques and compositions will be inexpensive, yet completely safe and suitable for human consumption or in vivo therapeutic uses. There also exists a need for new techniques and compositions suitable for depressing the freezing point or inhibiting freezing in non-organic systems, such as in deicing treatments. The present invention fulfills these and other needs.

SUMMARY OF THE INVENTION

The eastern spruce budworm, *Choristoneura fumiferana*, and western spruce budworm, *Choristoneura occidentalis*, are freeze-tolerant pests of North American forests. A defense against freezing is the thermal hysteresis (TH) activity of their hemolymph, which allows the insects to depress their freezing points in the presence of ice or ice nucleators. This activity is quantified as the temperature difference (°C.) between the freezing and melting points of a solution containing ice. Hemolymph from spruce budworm larvae demonstrates a freezing point depression of greater than 4° C.

This invention provides for the nucleic acid molecules that encode the proteins responsible for the thermal hysteresis in Choristoneura larvae, such as the nucleic acid of SEQ ID NO:1. The invention also provides for an isolated nucleic acid encoding an antifreeze protein where the protein can be defined as follows: having a calculated molecular weight of between 7 and 15 kDa; having a thermal hysteresis activity greater than about 1.5° C. at a concentration of about 1 mg/mL; and, specifically binding to an antibody raised against antifreeze proteins or antigenic fragments thereof selected from the group consisting of SEQ ID NO:2 and SEQ ID NO:3, or, having at least 60% amino acid sequence identity to an antifreeze protein selected from the group consisting of SEQ ID NO:2 and SEQ ID NO:3. In a preferred embodiment, the isolated nucleic acid encodes a protein with a calculated molecular weight between about 8 and 12 kDa. In a preferred embodiment, the nucleic acid encodes a protein with a thermal hysteresis activity that is greater than 2° C. at a concentration of about 1 mg/mL. In a preferred embodiment, the nucleic acid encodes a protein with at least 80% sequence identity to an antifreeze protein selected from the group consisting of SEQ ID NO:2 and SEQ ID NO:3. In a further embodiment, the invention provides for a nucleic acid encoding a protein with the sequence listed in SEQ ID NO:2 and SEQ ID NO:3. In another embodiment, the isolated nucleic acid encodes an antifreeze protein found in insects, and in a preferred embodiment that insect is a Choristoneura sp. The invention also provides for an isolated nucleic acid which specifically hybridizes to SEQ ID NO:1 under stringent conditions. The invention further provides for an isolated nucleic acid from a purified Choristoneura sp. antifreeze protein which specifically binds to an antibody directed against antifreeze proteins selected from the group consisting of SEQ ID NO:2 and SEQ ID NO:3.

The invention provides for THP proteins, including the recombinant proteins derived from the nucleic acids of this invention. The THP precursor protein (SEQ ID NO:2) has an N-terminal 18 residue signal sequence (SEQ ID NO:11) which is cleaved to generate mature THP protein (SEQ ID NO:3), see FIG. 2, which indicates the cDNA (SEQ ID NO:17) and corresponding amino acid sequence of spruce budworm THP.

The invention also provides for antibodies raised against the proteins of this invention and antibodies that bind to the proteins of this invention. The invention provides for antibodies specifically imnmunoreactive under immunologically reactive conditions to an antifreeze protein comprising SEQ ID NO:2 and SEQ ID NO:3. The invention also provides for an antibody, specifically immunoreactive under immunologically reactive conditions, to an antifreeze protein comprising the protein encoded by the nucleic acid of claim 1.

In a further embodiment of this invention, transformed yeast, bacteria and transgenic organisms are provided for. Many frozen foodstuffs suffer from formation of ice crystals due to sustained subfreezing temperatures or repeated freeze-thaw cycles. The presence of the THP of this invention will provide for longer shelf-life make these foodstuffs more palatable. Transgenic animals and plants are envisioned as better surviving sub-freezing temperatures. The invention provides for an organism into which an exogenous nucleic acid sequence which specifically hybridizes under stringent conditions to SEQ ID NO:1 or the nucleic acid of claim 1 has been introduced, and the organism translates the exogenous nucleic acid into an antifreeze protein. Also provided for is an organism with an exogenous nucleic acid sequence which is translated into an antifreeze protein that is expressed externally from the organism. In a preferred embodiment, the organism is a fish. In further preferred embodiments, organism is a fish is kept in a salt-water environment, or, the fish is a member of the family Salmonidae. In other preferred embodiments, the organism can be a plant, a fungus, a yeast or a bacteria. In another embodiment, if the organism is a yeast, it can be selected from the group consisting of Torulopsis holmil, Saccharomyces fragilis, Saccharomyces cerevisiae, Saccharomyces lactis, and Candida pseudotropicalis. In another embodiment, if the organism is a bacterium, it can be selected from the group consisting of Escherichia coli, Streptococcus cremoris, Streptococcus lactis, Streptococcus thermophilus, Leuconostoc citrovorum, Leuconostoc mesenteroides, Lactobacillus acidophilus, Lactobacillus lactis, Bifidobacterium bifidum, Bifidobacteriu breve, and Bifidobacterium longum.

The invention provides for a method for decreasing the freezing point of an aqueous solution involving the addition of an antifreeze protein to the aqueous solution. In a preferred embodiment, the method involves the addition of the antifreeze protein encoded by the nucleic acid of claim 1 to the aqueous solution. In other preferred embodiments, the aqueous solution is applied to an organism; the antifreeze protein is produced by recombinant means; the antifreeze protein can specifically bind to the antibody of claim 13 or claim 14; the antifreeze protein is selected from the group consisting of SEQ ID NO:2 and SEQ ID NO:3; and, the antifreeze protein is encoded by a nucleic acid molecule which specifically hybridizes to the nucleic acid of SEQ ID NO:1.

In addition, it is contemplated that the addition of the THP of this invention to aqueous solutions may better preserve organs and other biologicals in transit.

There also exists a need for new techniques and compositions suitable for depressing the freezing point or inhibiting freezing in non-organic systems, such as in deicing treatments.

A further understanding of the nature and advantages of the present invention may be realized by reference to the remaining portions of the specification, the figures and claims.

BRIEF DESCRIPTION OF THE FIGURES

FIG. 2 indicates the cDNA (SEQ ID NO:17) and corresponding amino acid sequence (SEQ ID NO:2) of spruce budworm THP.

DETAILED DESCRIPTION OF THE INVENTION

Figure 1:
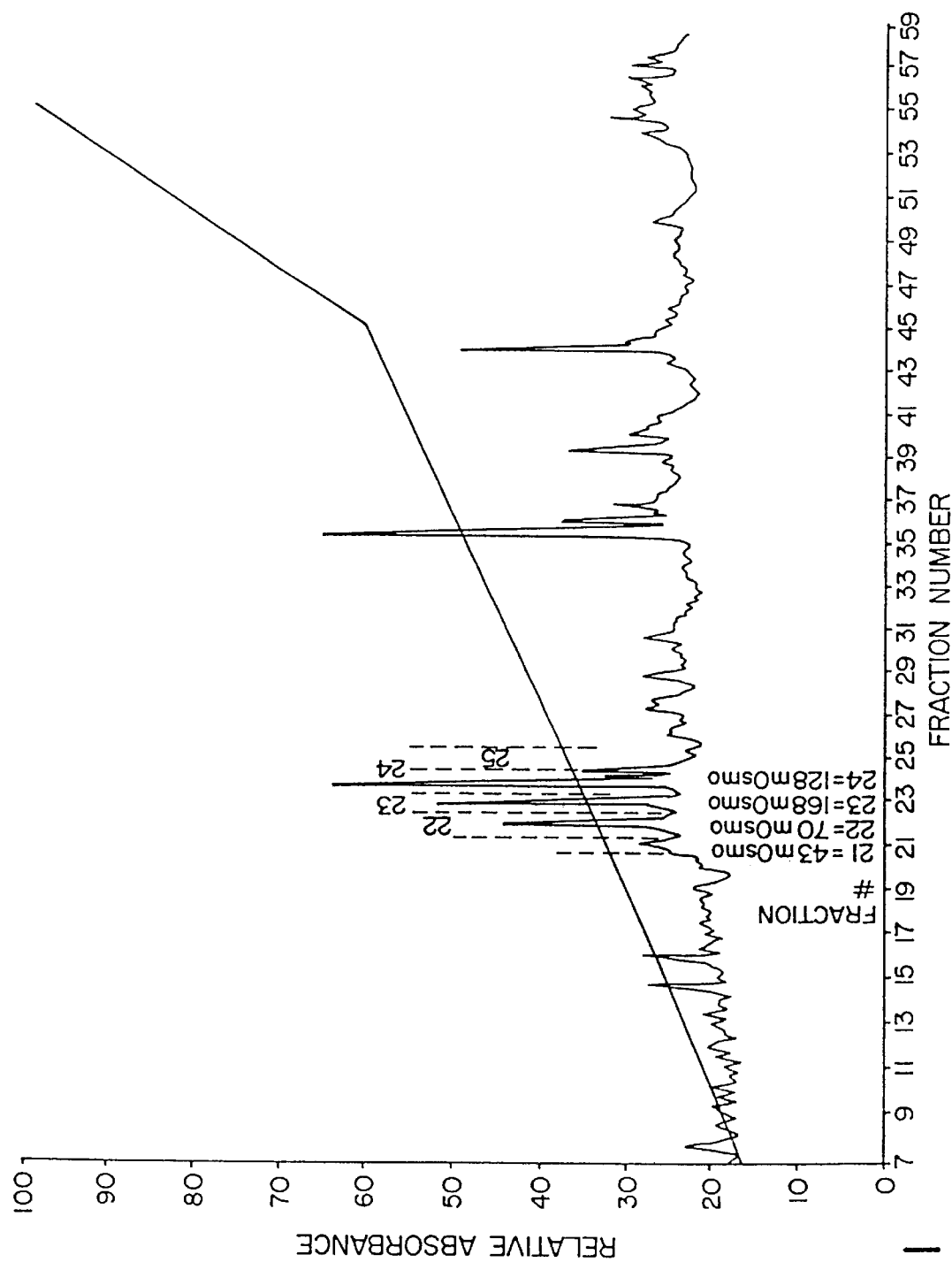
FIG. 1 is an elution profile of an HPLC C18 reversed-phase column onto which was loaded a mixture of proteins from second instar larvae of spruce budworm that had been previously sized on a Sephadex G-75 column (see text).

This invention relates to isolated nucleic acid sequences encoding a novel class of antifreeze proteins (THP). The procedure for obtaining natural THP genes generally involves constructing or obtaining gene libraries from Choristoneura sp., such as C. fumiferana and C. occidentalis, detecting and isolating the desired gene, cloning it, and expressing it in a suitable host cell and then purifying the expressed protein. The natural protein can be used without modification or it can be modified in a variety of ways without affecting its TH activity.

All publications, patents and patent applications cited herein are hereby expressly incorporated by reference for all purposes.

Hew, et al., reported that a crude preparation of a THP from C. fumiferana resembled a THP from the fish Hemitripterus americanus (sea raven) in terms of its high cystine content, its similar molecular weight (~13 kDa) and its antigenic cross-reactivity with sea raven THP. The novel C. fumiferana THPs of the invention differ from the protein described by Hew, et al., in at least two ways. First, its molecular weight is approximately 9 kDa. Second, it does not cross-react with polyclonal anti-sea raven antiserum (Slaughter, D., et al., Antifreeze proteins from the sea raven, Hemitripterus americanus, J. Biol. Chem. 256: 2022–2026 (1981); gift from Dr. Choy Hew, University of Toronto). Thus, the Hew et al. preparation is distinct from the novel THPs of the invention.

The THPs of the invention are more active than any purified antifreeze protein published to date. The freezing point depression provided by the THPs of the invention are several times greater than that provided by fish AFPs (THPs) or by T. molitor THP as prepared by Patterson, as described in Patterson, J., et al., The role of the thermal hysteresis factor in Tenebrio molitor larvae, J. Exp. Biol. 74: 37–45 (1978).

However, like fish antifreeze proteins, Choristoneura THP appears to act by an adsorption-inhibition mechanism. Ice crystals in the presence of THP stop growing until the non-equilibrium freezing point is exceeded. At that point, the ice crystals burst forth from the crystal nucleator to form a solid mass of ice principally along the a-axis and the ice fronts are broad and smooth. In contrast, once the freezing point is exceeded in the presence of fish AFPs, myriad ice spicules burst out along and parallel to the c-axis.

In addition, similar to fish AFP (DeVries, *Annu. Rev. Physiol.* 45:245 (1983), the relationship between TH activity and THP concentration is hyperbolic. However, the ice crystals formed in the presence of THP are unusual in that they have a pronounced curvature of their surfaces. In contrast, ice crystals generated by fish AFP Types I and III are hexagonal bipyramids with flat, well-defined facets.

The purified, expressed THP protein can be directly added to an aqueous solution to depress the freezing point or in another embodiment, transformed organisms that express the antifreeze proteins can be added to items which will be stored frozen, such as frozen desserts. In yet another embodiment, the transformed organisms, i.e., fish, plants and yeast, need not express the THP proteins extracellularly but the presence of a THP gene and intracellular protein confers to them the increased ability to survive freezing temperatures. For example, a transformed organism can be a saltwater fish. Transformed salt-water fish can include members of the family Salmonidae, halibut, sablefish or any edible saltwater species not having any or sufficient levels of antifreeze proteins. Plants transformed with THP sequences can include grapes, oilseed plants such as canola, grains, citrus and sugar cane.

I. DEFINITIONS

The term "antibody" refers to a polypeptide substantially encoded by an immnunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, FUNDAMENTAL IMMUNOLOGY, 3RD ED., W. E. Paul, ed., Raven Press, N.Y. (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

An "antifreeze protein antibody" is an antibody or antibody fragment that specifically binds an antifreeze protein of this invention or a subsequence thereof.

The term "antifreeze protein" refers to a protein found in the body fluids of some poikilothermic organisms, such as Choristoneura sp. such as *C. fumiferana* or *C. occidentalis*, the *Tenebrio molitor* mealworm and plants which have the commonly known property that they reduce non-colligatively the freezing point of water. THP are also known as "thermal hysteresis proteins." As used herein, "antifreeze proteins" or "THP" includes chemically synthesized and recombinantly produced polypeptides having a protein sequence with substantial similarity to a naturally occurring antifreeze protein and retaining the properties of an antifreeze polypeptide.

The term "decreasing the freezing point of an aqueous solution" refers to lowering the temperature of an aqueous solution at which ice crystals form. The decrease in freezing point depends both on the composition used to decrease the freezing point and its concentration in the aqueous solution. The freezing point depression increases as the antifreeze composition is added to the aqueous solution, until a characteristic concentration is achieved. The further addition of antifreeze chemicals, such as ethylene glycol to aqueous solutions will either result in insolubility of the antifreeze composition or serve to increase the freezing point of the mixture. On the other hand, the further addition of the THP of this invention does not affect the decreased freezing point of the solution.

The freezing point of a solution with a THP protein is defined as the temperature at which the sample being measured, which contains an ice crystal nucleator, becomes a solid mass of ice. The ice crystals can form spontaneously or expand from an ice nucleator. Spontaneous formation of a solid mass of ice without a nucleator is typically termed the "supercooling ability" of the THP. Because of the absence of an ice nucleator to initiate the ice formation process, supercooling can occur at much lower temperatures.

In addition to inspecting visually ice crystal formation, a thermal hysteresis assay can measure the difference between the freezing and melting points of a solution. The melting point of a solution is the temperature at which there is only one ice crystal left in a solution (see, infra, for a more complete description of TH activity).

The phrase "expressed externally" in the context of a recombinant protein refers to the ability of the transformed cell to synthesize and direct the protein into the extracellular matrix. The extracellular matrix can be the interstitial space between cells in a multicellular organism, bacterial broth or tissue culture media. With bacteria, external expression can also include expression of the recombinant protein into the periplasm of the bacteria. External expression can be by any means, e.g., secretory and transport vesicles, expression as a membrane protein, etc.

The terms "sequence identity," "sequence similarity" and "homology" in the context of this invention mean that two peptide sequences, when optimally aligned, such as by the programs GAP or BESTFIT using default gap weights, share at least 40 percent sequence identity, preferably at least 50 percent sequence identity, and most preferably at least 60 percent sequence identity. "Percentage amino acid sequence identity" refers to a comparison of the amino acid sequences of two polypeptides which, when optimally aligned, have approximately the designated percentage of the same amino acids. For example, "60% sequence identity" and "60% homology" refer to a comparison of the amino acid sequences of two polypeptides which when optimally aligned have 60% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The term "immunologically reactive conditions" refers to an environment in which antibodies can bind to antigens. Typically, this is an immunological binding assay.

The term "isolated," when applied to a nucleic acid or protein, denotes that the nucleic acid or protein is essentially free of other cellular components with which it is associated in the natural state. It is preferably in a homogeneous state, although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified.

In particular, an isolated antifreeze protein gene is separated from open reading frames which flank the gene and encode proteins other than the antifreeze protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid molecule" or "nucleic acid sequence" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, and mRNA encoded by a gene.

The phrase "exogenous nucleic acid" generally denotes a nucleic acid that has been isolated, cloned and ligated to a nucleic acid with which it is not combined in nature, and/or introduced into and/or expressed in a cell or cellular environment other than the cell or cellular environment in which said nucleic acid or protein may typically be found in nature. The term encompasses both nucleic acids originally obtained from a different organism or cell type than the cell type in which it is expressed, and also nucleic acids that are obtained from the same cell line as the cell line in which it is expressed.

The phrase "a nucleic acid sequence encoding" refers to a nucleic acid which contains sequence information for a structural RNA such as rRNA, a tRNA, or mRNA which encodes the primary amino acid sequence of a specific protein or peptide, or a binding site for a trans-acting regulatory agent. This phrase specifically encompasses degenerate codons (i.e., different codons which encode a single amino acid) of the native sequence or sequences which may be introduced to conform with codon preference in a specific host cell.

The term "recombinant means" refers to techniques where proteins are isolated, the cDNA sequence coding the protein identified and inserted into an expression vector. The vector is then introduced into a cell and the cell expresses the protein. Recombinant means also encompasses the ligation of coding or promoter DNA from different sources into one vector for expression of a fusion protein, constitutive expression of a protein, or inducible expression of a protein.

The phrase "specifically or selectively binds to an antibody" or "specifically immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised against the THP of this invention or to the partially encoded sequence depicted in SEQ ID NO:2 or SEQ ID NO:3 can be selected to specifically immunoreact with full length protein and not with other proteins except perhaps to polymorphic variants. As described below, a variety of inmmunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) ANTIBODIES, A LABORATORY MANUAL, Cold Spring Harbor Publications, New York ("Harlow and Lane"), for a description of immunoassay formats and conditions that can be used to determine specific immunoreactivity. Typically a specific or selective reaction will be at least twice background signal or noise and more typically more than 10 to 100 times background.

The term "specifically hybridizing" refers to a nucleic acid probe that hybridizes, duplexes or binds to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., MOLECULAR CLONING: A LABORATORY MANUAL (2ND ED.), Vols. 1–3, Cold Spring Harbor Laboratory, (1989) ("Sambrook"), which is incorporated herein by reference, or CURRENT PROTOCOLS IN MOLECULAR BIOLOGY, F. Ausubel et al., ed. Greene Publishing and Wiley-Interscience, New York (1987) ("Ausubel").

"Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) LABORATORY TECHNIQUES IN BIOCHEMISTRY AND MOLECULAR BIOLOGY—HYBRIDIZATION WITH NUCLEIC ACID PROBES part I chapter 2 "overview of principles of hybridization and the strategy of nucleic acid probe assays", Elsevier, N.Y. Generally, highly stringent hybridization and wash conditions are selected to be about 5° C. lower than the thermal melting point ($T_m$) for the specific sequence at a defined ionic strength and ph. The $T_m$ is the temperature, under defined ionic strength and pH, at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see Sambrook for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The term "thermal hysteresis activity" or "TH activity" refers to the ability to alter the temperature difference (° C.) between the freezing and melting points of a solution containing ice. Preferably, TH activity is be measured by observation of ice crystal formation in a nanoliter osmometer following the procedure set forth in Lawson & Semler, Proc. Nat'l Acad. Sci. USA 88:9919 (1991). Alternatively, TH activity can be determined according to the method described in deVries, METHODS IN ENZYMOLOGY, VOL. 127, Packer (ed.), Academic Press, New York (1986) or a variation thereof.

For example, in the present invention, the TH activity of the native Choristoneura sp., such as C. fumiferana or C. occidentalis, THP from hemolymph at 1 mg/mL is greater than approximately 4° C. The TH activity of the recombinant THP of this invention at 1 mg/mL is about 4° C. or less. More preferably, the TH activity is lower than about 3° C. Most preferably, the TH activity is between 1.5 and 3° C. It is hypothesized that the small differences between the TH activity of the native THP and the recombinant THP is due to non-optimized folding in the bacteria-derived recombinant proteins. When properly folded, it is expected that the TH activities of the recombinant THP will be similar to that of the native THP.

II. NUCLEIC ACIDS ENCODING THP

A. General Techniques

The nucleic acid compositions of this invention, whether RNA, cDNA, genomic DNA, or a hybrid of the genetic recombinations, may be isolated from natural sources or may be synthesized in vitro. The nucleic acids claimed may be present in transformed cells, in a transformed cell lysate, or in a partially purified or substantially pure form.

Techniques for nucleic acid manipulation of genes encoding the antifreeze protein such as generating libraries, subcloning into expression vectors, labeling probes, DNA hybridization, and the like are described generally in Sambrook.

Nucleic acids and proteins are detected and quantified herein by any of a number of means well known to those of skill in the art. These include analytical biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassay (RIAs), enzyme-linked immunosorbent assays (ELISAs), immunofluorescent assays, and the like. The detection of nucleic acids proceeds by well known methods such as Southern analysis, northern analysis, gel electrophoresis, PCR®, radiolabeling, scintillation counting, and affinity chromatography.

B. Isolation of Nucleic Acids Encoding2 THP

Methods of isolating total DNA or mRNA are well known to those of skill in the art. For example, methods of isolation and purification of nucleic acids are described in detail in Chapter 3 of LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, P. Tijssen, ed. Elsevier, N.Y. (1993) ("Tijssen").

1. Preparation and Screening of DNA Libraries

There are numerous methods for isolating the DNA sequences encoding the antifreeze protein of this invention. For example, DNA can be isolated from a genomic or cDNA library using labeled oligonucleotide probes having sequences complementary to the sequences or subsequences disclosed herein (SEQ ID NOs:4 or 5). Such probes can be used directly in hybridization assays to isolate DNA encoding THP isoforms. Alternatively probes can be designed for use in amplification techniques such as PCR®, and DNA encoding THP may be isolated by using methods such as PCR® (see infra).

To prepare a cDNA library, mRNA is isolated from Choristoneura sp. larvae or from larval cells grown in tissue culture is reverse transcribed from the mRNA according to procedures well known in the art and inserted into vectors. The vectors are transfected into a recombinant host for propagation, screening and cloning. Methods for making and screening cDNA libraries are well known. See Gubler and Hoffman, Gene 25:263–269, (1983) and Sambrook.

To make a genomic library, total DNA is extracted and purified from larvae by well-known methods (see, for example, Sambrook). DNA of appropriate size is produced by known methods, such as mechanical shearing or enzymatic digestion, to yield DNA fragments, e.g., of about 12 to 20 kb. The fragments are then separated by gradient centrifugation from undesired sizes and are inserted in bacteriophage-λ or other vectors. These vectors and phage are packaged in vitro, as described, for example, in Sambrook. Recombinant phage are analyzed by plaque hybridization as described in Benton & Davis, *Science*, 196:180 (1977). Colony hybridization is carried out as generally described in M. Grunstein, et al., *Proc. Natl. Acad. Sci. USA*., 72:3961–3965 (1975).

DNA encoding THP can be identified in either cDNA or genomic libraries by its ability to hybridize with nucleic acid probes, for example, SEQ ID NO:4, SEQ ID NO:5, SEQ ID NO:13, SEQ ID NO:14, SEQ ID NO:15 or SEQ ID NO:16, on Southern blots. Once identified, these DNA regions are isolated by standard methods familiar to those of skill in the art. Alternatively, RNA encoding antifreeze protein may be identified by its ability to hybridize to nucleic acid probes in northern blots, see Sambrook.

Oligonucleotides for use as probes are chemically synthesized according to the solid phase phosphoramidite triester method first described by Beaucage and Carruthers using an automated synthesizer, as described in Needham-VanDevanter, D. R., et al., *Nucleic Acids Res.* 12:6159–6168 (1984). Purification of oligonucleotides is by either native acrylamide gel electrophoresis or by anion-exchange HPLC as described in Pearson, J. D. and Regnier, F. E., *J. Chrom.* 255:137–149 (1983). The sequence of the synthetic oligonucleotide can be verified using the chemical degradation method of Maxam, A. M. and Gilbert, W., METHODS IN ENZYMOLOGY, 65:499–560, (Grossman, L. and Moldave, D., eds.), Academic Press, New York (1980).

Other methods known to those of skill in the art may also be used to isolate DNA encoding the antifreeze protein. See Sambrook and Ausubel for descriptions of other techniques that can be utilized for the isolation of DNA encoding specific protein molecules.

2. Amplification of Nucleic Acids Encoding THP

The nucleic acid sequence (SEQ ID NO:1) and protein sequence information (SEQ ID NO:2 and SEQ ID NO:3) can be used to design PCR primers which can be used to identify antifreeze protein sequences, such as spruce budworm THP. PCR primer pairs that are known to generate Choristoneura sp. THP sequences, such as: SEQ ID NO:4 and SEQ ID NO:5; SEQ ID NO:13 and SEQ ID NO:14; and, SEQ ID NO:15 and SEQ ID NO:16, can be used to directly amplify new antifreeze protein species and isoforms. In one isoform of *C. fumiferana*, the SEQ ID NO:4 and SEQ ID NO:5 primer pair amplifies full length THP cDNA coding sequence.

PCR primers such as SEQ ID NO:13 and SEQ ID NO:14 can be used to directly amplify new antifreeze protein species and isoforms or to generate a DNA probe that would include signal sequence, the mature protein coding region and much of the 3' untranslated region, i.e., the poly-A attachment site. These primers, whether used to directly amplify new THP species, used directly as probes, or used to generate (by PCR amplification) longer DNA probes, will also hybridize to a wide variety of different THP species and isoforms, especially those including THP sequence variants that are better conserved in the signal sequence and 3'-untranslated region than in the mature protein coding region. These 23-mer primers have estimated Tms of 62° C.

PCR primers such as SEQ ID NO:15 and SEQ ID NO:16 can also be used to directly amplify new antifreeze protein species and isoforms or to generate a DNA probe that would include an internal subset of the THP coding sequence. In one isoform of *C. fumiferana*, the SEQ ID NO:15 and SEQ ID NO:16 primer pair amplifies a 191 base pair PCR product coding for an internal block of the mature THP protein. These primers have estimated Tms of 62° C. to 64° C.

PCR-generated oligonucleotides can be useful to identify and detect new antifreeze protein-encoding nucleic acid using different hybridization techniques and conditions. One of skill in the art will appreciate that whatever amplification method is used, if a quantitative result is desired, care must be taken to use a method that maintains or controls for the relative frequencies of the amplified nucleic acids. Suitable amplification methods include, but are not limited to: polymerase chain reaction, PCR® (PCR PROTOCOLS, A GUIDE TO METHODS AND APPLICATIONS, Innis, et al., Academic Press, Inc. N.Y., (1990) ("Innis")), ligase chain reaction (LCR) (see Wu and Wallace, *Genomics*, 4:560 (1989) ("Wu"), Landegren et al., *Science*, 241:1077 (1988) ("Landegren") and Barringer et al., *Gene* 89:117 (1990) ("Barringer"); transcription amplification (Kwoh et al., *Proc. Natl. Acad. Sci. USA*, 86:1173 (1989) ("Kwoh")); and, self-sustained sequence replication (Guatelli, et al., *Proc. Nat. Acad. Sci. USA*, 87:1874 (1990) ("Guatelli")).

All of the above methods can be used to prepare DNA encoding antifreeze protein. In PCR® techniques, oligonucleotide primers complementary to the two borders of the DNA region to be amplified are synthesized. The polymerase chain reaction is then carried out using the two primers (see, Innis). PCR® can be used in a variety of protocols to amplify, identify and isolate nucleic acids encoding THP. In these protocols, appropriate primers and probes for identifying and amplifying DNA encoding antifreeze protein are generated from analysis of the DNA sequences listed herein. For example, the oligonucleotides 5'-CATATGCAT<u>ATG</u>GATGGCTCGTGTACAAACAC-3' (SEQ ID NO:4) and 5'-AAGCTTAAGCTT<u>TTA</u>ATTAGCACTGAAAGTACA-3' (SEQ ID NO:5) can be used in a PCR protocol to identify and amplify different species and isoforms of THP cDNA. In one isoform of *C. fumiferana*, this primer pair amplifies full length THP cDNA coding sequence. Note that the underlined codons in SEQ ID NO:4 and SEQ ID NO:5 designate the initiation and termination codons, respectively, found in that THP isoform.

As discussed above, other examples of primer pairs used to identify and amplify different species and isoforms of THP include: the oligonucleotides 5'-TGAAGTGTTTAATGCTGATCATG-3' (SEQ ID NO:13) and 5'-CATTAGAGTAGCATAATGTAAGC-3' (SEQ ID NO:14); and, 5'-TCCAAGTGCGAAAAATCGACG-3' (SEQ ID NO:15) and 5'-GCTGATGGAGCAGGTACACC-3' (SEQ ID NO:16).

While PCR-amplified sequences can also be labeled and used as detectable oligonucleotide probes, such nucleic acid probes can be generated using any amplification technique well known in the art, as described above. Also using well known techniques, the labeled amplified DNA can be used as probes to further identify and isolate additional antifreeze protein species or isoforms from various cDNA or genomic libraries.

Another approach for DNA amplification is the "RACE" technique. Briefly, this technique involves using PCR® to amplify a DNA sequence using a random 5' primer and a defined 3' primer (5' RACE) or a random 3' primer and a defined 5' primer (3' RACE). The amplified sequence is then subcloned into a vector where it is then sequenced using standard techniques. The RACE method is well known to those of skill in the art and kits to perform RACE are commercially available (e.g. 5' RACE System, GIBCO BRL, Grand Island, N.Y., USA).

3. Cloning of THP-encoding Inserts into Bacteria

As described above, to prepare and screen genomic DNA total DNA is fragmented and inserted into bacteriophage. Once inserts containing antifreeze nucleic acid sequence of interest have been identified (by PCR, hybridization or the like), they are excised out of λ phage vectors and inserted into bacterial vectors for expansion. Typically, suitable bacterial vectors are known to practitioners in the art and are commercially available. The most suitable vector may depend on the bacteria to be used, the size of the insert, the method of detection of bacteria which contain the insert of interest and the preference of the practitioner.

To simplify identification of colonies of bacteria transformed with vectors containing the inserts, many vectors have restriction enzyme sites or other splicing sites located within a coding sequence for an enzyme, in particular, β-galactosidase. If an insert has successfully been inserted into the vector at the restriction or splicing sites, the enzyme is inactivated. After transformation of the bacteria with the vector (see, infra), colonies grown in the presence of isopropyl β-D-thiogalactoside (IPTG) (a substrate β-galactosidase) appear white, while the colonies derived from a bacteria which did not incorporate the insert appear blue. Thus, if the frequency of ligation of the insert into the vector was low, one can pick the few colonies that contain inserts over the many that will not.

The vectors are then introduced into variants of *Escherichia coli*. Methods used to introduce foreign DNA into bacterial cells are known to those of skill in the art, but the most frequently used are electroporation and heat shock of competent cells. Most typically, competent *E. coli* are provided commercially (for example from Invitrogen, San Diego, Calif.). Alternatively, the bacteria can be made competent to take up foreign DNA by techniques well known in the art (Sambrook). To introduce the vectors containing the insert of interest into bacteria, the competent bacteria undergo a heat shock process. Briefly, the bacteria are held in an ice water bath and after the DNA has been added, the temperature of the bacteria is raised to 40–50° C., preferably 42° C. The bacteria are returned to the ice bath and then cultured. For a more detailed description of introducing DNA into bacteria see Sambrook.

The bacterial cultures are grown and then plated out on agar. Typically, the vector encodes a gene which confers resistance to an antibiotic to the transformed bacteria. Therefore, bacteria which have taken up the vector survive and form colonies on agar plates permeated with the antibiotic. The surviving colonies can be used to incubate broth and expanded into large cultures of transformed bacteria.

Plasmids and other vectors can be purified from bacterial lysates by methods well known in the art. Many commercial suppliers sell kits for purifying small circularized DNA (plasmids) from total bacterial DNA. These kits are easy to use and, by following the manufacturer's instructions, the yield is usually quite high.

4. Sequencing of THP DNA

Sequencing of newly isolated DNA will identify and characterize THP nucleic acid of the invention, this nucleic acid encoding THP species or allelic variations, the antifreeze proteins of the invention. A protein can be considered a THP protein isoform if it has at least 60% amino acid sequence identity to the *Choristoneura fumiferana* THP identified by SEQ ID NO:2 and SEQ ID NO:3.

Antifreeze protein coding sequences can be sequenced while they are still present as inserts in vectors or as inserts released and isolated from the vectors. THP-encoding inserts can be released from the vectors by restriction enzymes or amplified by PCR. For sequencing of the inserts to discover which inserts contain full length antifreeze coding sequences, primers based on the N- or C-terminus, such as those of SEQ ID NO:4 and SEQ ID NO:5, or insertion points in the original λ-phage, can be used as primers. Most preferably, additional primers are synthesized to provide for overlapping sequences. Typically, dideoxy sequencing is done (Sequenase®, U.S. Biochemical). However, other kits and methods are available and known to those of skill in the art.

As an alternative to the bacterial cloning described above, the positive λ-phage plaques from the cDNA library can be subjected to in vivo excision with helper phage, for example R408 (Stratagene). The double stranded DNA can then be purified and sequenced or amplified by PCR using primers derived from the λ-phage.

C. Nucleic Acid Hybridization Techniques

The hybridization techniques disclosed herein can be utilized to identify, isolate and characterize genes and gene products (i.e., mRNA) encoding for the antifreeze proteins of the invention, including different THP species and allelic variations.

A variety of methods for specific DNA and RNA measurement using nucleic acid hybridization techniques are known to those of skill in the art. See NUCLEIC ACID HYBRIDIZATION, A PRACTICAL APPROACH, Ed. Hames, B. D. and Higgins, S. J., IRL Press, 1985; Gall and Pardue, *Proc. Natl. Acad. Sci., U.S.A*. 63:378 (1969); John, et al., *Nature* 223:582 (1969); and Sambrook. The selection of a hybridization format is not critical.

For example, one method for evaluating the presence or absence of DNA encoding antifreeze protein in a sample involves a Southern transfer. Briefly, the digested bacterial genomic DNA is run on agarose slab gels in buffer and transferred to membranes. Hybridization is carried out using nucleic acid probes. For the THP of this invention, the nucleic acid probes can be designed based on conserved nucleic acid sequences amongst the class of proteins. Preferably nucleic acid probes are 20 bases or longer in length. (See Sambrook for methods of selecting nucleic acid probe sequences for use in nucleic acid hybridization.) Visualization of the hybridized portions allows the qualitative determination of the presence or absence of DNA encoding antifreeze protein.

Similarly, a northern transfer can be used for the detection of mRNA encoding antifreeze protein. For example, mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern transfers, labeled probes or PCR can be used to identify the presence or absence of antifreeze protein-encoding nucleic acid.

Sandwich assays are commercially useful hybridization assays for detecting or isolating nucleic acid sequences. Such assays utilize a "capture" nucleic acid covalently immobilized to a solid support and a labeled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography or autofluorography with $^{3}H$, $^{125}I$, $^{35}S$, $^{14}C$, or $^{32}P$-labeled probes or the like. Other labels include ligands which bind to labeled antibodies, fluorophores, chemiluminescent agents, enzymes, and antibodies which can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The label may also allow indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label (for example, see Tijssen, pp. 9 to 20).

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including PCR, LCR, Qβ-replicase amplification and other RNA polymerase mediated techniques (e.g., NASBA) are found in Berger, Sambrook, and Ausubel, as well as Mullis et al., (1987); U.S. Pat. No. 4,683,202; Arnheim & Levinson, C&EN 36–47 (1990); Lomell et al., *J. Clin. Chem.*, 35:1826 (1989); Van Brunt, *Biotechnology*, 8:291–294 (1990); Wu and Wallace, *Gene* 4:560 (1989); Sooknanan and Malek, *Biotechnology* 13:563–564 (1995); Innis; Kwoh; Guatelli; Landegren; and Barringer. Improved methods of cloning in vitro amplified nucleic acids are described in Wallace et al., U.S. Pat. No. 5,426,039. Other methods recently described in the art are the nucleic acid sequence based amplification (NASBA™, Cangene, Mississauga, Ontario) and Q Beta Replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Oligonucleotides for use as probes, e.g., in vitro amplification methods, as gene probes in diagnostic methods, or as inhibitor components (see below) are typically synthesized chemically according to the solid phase phosphoramidite triester method described by Beaucage and Caruthers, e.g., using an automated synthesizer, as described in Needham-VanDevanter. Purification of oligonucleotides, where necessary, is typically performed by native acrylamide gel electrophoresis or by anion-exchange HPLC as described in Pearson and Regnier. The sequence of the synthetic oligonucleotides can be verified using the chemical degradation method of Maxam and Gilbert.

It will be appreciated that nucleic acid hybridization assays can also be performed in an array-based format. In this approach, arrays bearing a multiplicity o f different "probe" nucleic acids are hybridized against a target nucleic acid. In this manner a large number of different hybridization reactions can be run essentially "in parallel". This provides rapid, essentially simultaneous, evaluation of a wide number of reactants. Methods of performing hybridization reactions in array based formats are well known to those of skill in the art (see, e.g., Jackson, et al., *Nature Biotechnology* 14:1685 (1996), and Chee, et al., *Science* 274:610 (1995)).

An alternative means for determining the level of expression of a gene encoding a protein is in situ hybridization. In situ hybridization assays are well known and are generally described in Angerer, et al., *Methods Enzymol.*, 152:649 (1987). In an in situ hybridization assay, cells are fixed to a solid support, typically a glass slide. If DNA is to be probed, the cells are denatured with heat or alkali. The cells are then contacted with a hybridization solution at a mode rate temperature to permit annealing of labeled probes specific to the nucleic acid sequence encoding the protein. The probes are preferably labeled with radio isotopes or fluorescent reporters.

D. Expression of THP

After the coding, region of an antifreeze protein gene has been identified, the expression of natural or synthetic antifreeze-encoding nucleic acids can be achieved by operably linking the coding region of an antifreeze protein gene to a promoter (which is either constitutive or inducible), incorporating the construct into an expression vector, and introducing the vector into a suitable host cell. Typical vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman and Smith, *Gene* 8:81 (1979); Roberts, et al., *Nature* 328:731 (1987); Berger and Kimmel, GUIDE TO MOLECULAR CLONING TECHNIQUES, METHODS IN ENZYMOLOGY, Vol 152, Academic Press, Inc., San Diego, Calif. ("Berger"); Schneider, B., et al., *Protein Expr. Purif.* 6435:10 (1995); Sambrook and Ausubel. Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia Biotech (Piscataway, N.J.), CLONTECH Laboratories, Inc. (Palo Alto, Calif.), Aldrich Chemical Company (Milwaukee, Wis.), GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill.

The nucleic acids (e.g., promoters and vectors) used in the present method can be isolated from natural sources, obtained from such sources as ATCC or GenBank libraries, or prepared by synthetic methods. Synthetic nucleic acids can be prepared by a variety of solution or solid phase methods. Detailed descriptions of the procedures for solid phase synthesis of nucleic acids by phosphite-triester, phosphotriester, and H-phosphonate chemistries are widely available. See, for example, Itakura, U.S. Pat. No. 4,401, 796; Carruthers, et al., U.S. Pat. Nos. 4,458,066 and 4,500, 707; Beaucage and Carruthers; Matteucci; Carruthers, et al., *Genetic Engineering* 4:1–17 (1982); Jones, chapter 2, Atkinson, et al., chapter 3, and Sproat, et al., chapter 4, in OLIGONUCLEOTIDE SYNTHESIS: A PRACTICAL APPROACH, Gait (ed.), IRL Press, Washington D.C. (1984); Froehler, et al., *Tetrahedron Lett.* 27:469–472 (1986); Froehler, et al., *Nucleic Acids Res.* 14:5399–5407 (1986); Sinha, et al., *Tetrahedron Lett.* 24:5843–5846 (1983); and Sinha, et al., *Nucl. Acids Res.* 12:4539–4557 (1984), which are incorporated herein by reference.

There are several well-known methods of introducing nucleic acids into bacterial cells, any of which may be used in the present invention (see Sambrook). These can include fusion of the recipient cells with bacterial protoplasts containing the DNA, DEAE dextran, infection with viral vectors, and the like.

The in vitro delivery of nucleic acids into bacterial hosts can be to any cell grown in culture. Contact between the cells and the genetically engineered nucleic acid constructs, when carried out in vitro, takes place in a biologically compatible medium. The concentration of nucleic acid varies widely depending on the particular application, but is generally between about 1 $\mu$M and about 10 mM. Treatment of the cells with the nucleic acid is generally carried out at physiological temperatures (about 37° C.) for periods of time of from about 1 to 48 hours, preferably of from about 2 to 4 hours.

Bacterial strains which can be used to express exogenous nucleic acid include *Escherichia coli, Streptococcus cremoris, Streptococcus lactis, Streptococcus thermophilus, Leuconostoc citrovorum, Leuconostoc mesenteroides, Lactobacillus acidophilus, Lactobacillus lactis, Bifidobacterium bifidum, Bifidobacteriu breve*, and *Bifidobacterium longum.*

In addition to bacterial expression systems, the THP of this invention can be expressed in other systems, in particular yeast and baculovirus, but also in mammalian and plant cells. The system used will depend on the lack of success in other systems, the ability to fold the THP properly, and the eventual use of the THP. For example, if the THP are to be used to protect bread dough yeast from freezing (see, U.S. Pat. No. 5,118,792), a yeast system will be used. If plants which can live through freezing temperatures are desired, transgenic techniques can be used to make transgenic plants. However, of course, the system used should give THP with comparable thermal hysteresis activity to that found in Choristoneura sp. larvae.

Yeast strains which can be used to express exogenous nucleic acid include *Torulopsis holmil, Saccharomyces fragilis, Saccharomyces cerevisiae, Saccharomyces lactis*, and *Candida pseudotropicalis.*

As an example of alternative expression systems, see International Publication WO 96/11586 (U.S. patent application Ser. No. 08/321,991, filed Oct. 12, 1994), incorporated herein by reference, which describes the use of fish AFP(THP)-transformed *Lactobacillus bulgaricus* and *Streptococcus thermophilus* to secrete AFP in order to prevent ice crystal formation in fermented frozen foods, in particular frozen yogurt, from freeze-thaw cycles when kept in frost-free freezers.

1. Preparation of Recombinant Vectors

To use isolated sequences in the above techniques, recombinant DNA vectors suitable for transformation of cells are prepared. Techniques for transforming a wide variety of animal and plant cells are well known and described in the technical and scientific literature. See, for example, Weising, et al., *Ann. Rev. Genet.* 22:421–477 (1988) for plant cells and Sambrook for animal and bacterial cells.

A DNA sequence coding for the desired antifreeze protein, for example a cDNA sequence encoding the full length THP, will preferably be combined with transcriptional and translational initiation regulatory sequences which will direct the transcription of the sequence from the gene in the cells or the intended tissues of the transgenic higher organism. A wide variety of well known transcriptional regulatory elements such as promoters and enhancers can also be included in the vectors selected to express a THP of the invention. Promoters which direct the THP of this invention in their native state can be identified by analyzing the 5' sequences of a genomic clone corresponding to the antifreeze protein genes described herein. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation.

In construction of recombinant expression cassettes of the invention, a promoter fragment, either related to the THP of this invention or heterologous to the THP, may be employed which will direct expression of the gene in all tissues of a transgenic organism. Such promoters are referred to herein as "constitutive" promoters and are active under most environmental conditions and states of development or cell differentiation. Examples of constitutive promoters of plants include the cauliflower mosaic virus (CaMV) 35S transcription initiation region, the 1'- or 2'-promoter derived from T-DNA of *Agrobacterium tumafaciens*, promoter of the tobacco mosaic virus and transcription initiation regions from various plant genes known to those of skill in the art.

Alternatively, the promoter may direct expression of the polynucleotide of the invention in a specific tissue (tissue-specific promoters) or may be otherwise under more precise environmental control (inducible promoters). Examples of tissue-specific plant promoters under developmental control include promoters that initiate transcription only in certain tissues, such as fruit, seeds, or flowers. The tissue specific E8 promoter from tomato is particularly useful for directing gene expression so that a desired gene product is located in fruits. Other suitable promoters include those from genes encoding embryonic storage proteins. Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on transformed cells. For example, the marker may encode antibiotic resistance, particularly resistance to kanamycin, G418, bleomycin and hygromycin.

Plants can be transformed using viral vectors, such as, for example, the tobacco mosaic virus, to express THP proteins of the invention. Selection and construction of vectors and techniques for transforming a wide variety of plant cells are well known, for example, see Hamamoto, et al., U.S. Pat. No. 5,618,699.

2. Production of Transgenic Organisms

DNA constructs of the invention may be introduced into the genome of a host organism by a variety of conventional techniques. For example, in plants, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. As discussed above, plant virus vectors such as tobacco mosaic virus containing the THP sequences of the invention can be used to innoculate a plant. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

*Agrobacterium tumefaciens*-mediated transformation techniques, including disarming and use of binary vectors, are well described in the scientific literature. See, for example Horsch, et al., *Science* 233:496 (1984), and Fraley, et al., *Proc. Nat'l. Acad. Sci. USA* 80:4803 (1983).

Transformed plant cells which are derived by any of the above transformation techniques can be cultured to regenerate a whole plant which possesses the transformed genotype and thus the desired phenotype, such as increased tolerance to freezing. The transformed plants of the invention can also be employed as "living factories" to express an antifreeze protein in substantial quantities. Such plant regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., PROTOPLASTS ISOLATION AND CULTURE, HANDBOOK OF PLANT CELL CULTURE, pp. 124–176, Macmillian Publishing Company, New York, 1983; and Binding, REGENERATION OF PLANTS, PLANT PROTOPLASTS, pp. 21–73, CRC Press, Boca Raton, 1985. Regeneration can also be obtained from plant callus, explants, organs, or parts thereof. Such regeneration techniques are described generally in Klee, et al., Ann. Rev. of Plant Phys. 38:467 (1987).

To produce a transgenic plant or animal, for example a salt-water fish, microinjection techniques are known in the art and well described in the scientific and patent literature. The introduction of DNA constructs into cells using polyethylene glycol precipitation is described in Paszkowski, et al., EMBO J. 3:2717 (1984). Electroporation techniques are described in Fromm, et al., Proc. Natl. Acad. Sci. USA 82:5824 (1985). Ballistic transformation techniques are described in Klein, et al., Nature 327:70 (1987).

III. DETECTION AND CHARACTERIZATION OF THE CLASS OF THP OF THIS INVENTION

By the assays described below, the THP of this invention share characteristics with a thermal hysteresis protein isolated from second larval instar *Choristoneura fumiferana* and *Choristoneura occidentalis* hemolymph. These assays are used to define whether other novel THP are sufficiently related to these prototype proteins so as to fall within the scope of this invention. The assays can also be pursued to detect and quantify THP proteins present in bacteria broth, tissue culture fluid and plant and animal tissues.

A. Detection of THP

Expressed THP may be detected or quantified by a variety of methods. Preferred methods involve the use of functional activity assays and immunological assays utilizing specific antibodies.

1. Antibodies

Methods of producing polyclonal and monoclonal antibodies are known to those of skill in the art. See, e.g., Coligan, CURRENT PROTOCOLS IN IMMUNOLOGY, Wiley/Greene, NY (1991); Stites et al. (eds.) BASIC AND CLINICAL IMMUNOLOGY (7th ed.) Lange Medical Publications, Los Altos, Calif., and references cited therein ("Stites"); Goding, MONOCLONAL ANTIBODIES: PRINCIPLES AND PRACTICE (2d ed.) Academic Press, New York, N.Y. (1986); Kohler and Milstein, Nature 256:495 (1975); and Harlow and Lane. Such techniques include antibody preparation by selection of antibodies from libraries of recombinant antibodies in phage or similar vectors. See, Huse et al., Science 246:1275 (1989) ("Huse"); and Ward et al., Nature 341:544 (1989).

To produce large amounts of antibodies for use in, for example, immunoaffinity purification, a number of immunogens may be used. Antifreeze protein from Choristoneura sp. or from the transformed cells as described in this invention are the preferred immunogens for the production of monoclonal or polyclonal antibodies. Naturally occurring antifreeze protein from other organisms may also be used either in pure or impure form. Synthetic peptides made using a fragment of antifreeze protein sequence described herein may also used as an immunogen for the production of antibodies to the protein. The peptides can be used alone or conjugated to another composition.

Methods of production of polyclonal antibodies are known to those of skill in the art. In brief, an immunogen is mixed with an adjuvant, as described above, and animals are immunized. The animal's immune response to the immunogen preparation is monitored by taking test bleeds and determining the titer of reactivity to the immunogen. When appropriately high titers of antibody to the immunogen are obtained, blood is collected from the animal and antisera are prepared. Further fractionation of the antisera to enrich for antibodies reactive to the protein can be done if desired. (See Harlow and Lane, supra).

Large amounts of monoclonal antibodies for use in immunoaffinity purification or immunoassays may be obtained by various techniques familiar to those skilled in the art. Briefly, spleen cells from an animal immunized with a desired antifreeze protein are immortalized, commonly by fusion with a myeloma cell (See, Kohler and Milstein, Eur. J. Immunol. 6:511 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for THP. The yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined in Huse.

The concentration of THP can be measured by a variety of immunoassay methods. For a review of immunological and immunoassay procedures in general, see Stites. Moreover, the immunoassays of the present invention can be performed in any of several configurations, which are reviewed extensively in ENZYME IMMUNOASSAY, E. T. Maggio, ed., CRC Press, Boca Raton, Fla. (1980); Tijssen; and Harlow and Lane, each of which is incorporated herein by reference.

For example, in order to produce antisera for use in an immunoassay for antifreeze protein, recombinant spruce budworm antifreeze protein, or immunogenic fragments thereof, are produced and isolated as described herein. An inbred strain of mice or rabbits is immunized with the polypeptide of SEQ ID NO:2 or SEQ ID NO:3, or its isoforms or immunogenic fragments thereof, using a standard adjuvant, such as Freund's adjuvant, and a standard immunization protocol. Alternatively, a synthetic peptide derived from the sequences disclosed herein and conjugated to a carrier protein can be used an immunogen. Polyclonal sera are collected and tittered against the THP in an immunoassay, for example, a solid phase immunoassay with the THP immobilized on a solid support. Polyclonal antisera with a titer of $10^4$ or greater are selected and tested for their cross reactivity against homologous proteins from other organisms and/or non-antifreeze protein, using a competitive binding immunoassay. Specific monoclonal and polyclonal antibodies and antisera will usually bind with a $K_D$ of at least about 0.1 mM, more usually at least about 1 $\mu$M, preferably at least about 0.1 $\mu$M or better, and most preferably, 0.01 $\mu$M or better.

2. Immunological Binding Assays.

In a preferred embodiment, THP are detected and/or quantified using any of a number of well recognized immunological binding assays (see, e.g., U.S. Pat. Nos. 4,366,241; 4,376,110; 4,517,288; and 4,837,168). For a review of the general immunoassays, see also METHODS IN CELL BIOLOGY Vol. 37. *Antibodies in Cell Biology*, Asai, ed. Academic Press, Inc. New York (1993); and Stites. Immunological binding assays (or immunoassays) typically utilize a "capture agent" to specifically bind to and often immobilize the analyte (in this case THP or a fragment thereof). The capture agent is a moiety that specifically binds to the analyte. In a preferred embodiment, the capture agent is an antibody that specifically binds to THP. The antibody (anti-THP) may be produced by any of a number of means well known to those of skill in the art and as described above.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled THP polypeptide or a labeled anti-THP antibody. Alternatively, the labeling agent may be a third moiety, such as another antibody, that specifically binds to the antibody/THP complex.

In a preferred embodiment, the labeling agent is a second THP antibody bearing a label. Alternatively, the second THP antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al., *J. Immunol.* 111:1401–1406 (1973), and Akerstrom, et al., *J. Immunol.* 135:2589–2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

a. Non-Competitive Assay Formats.

Immunoassays for detecting THP may be either competitive or noncompetitive. Noncompetitive immunoassays are assays in which the amount of captured analyte (in this case THP) is directly measured. In one preferred "sandwich" assay, for example, the capture agent (anti-THP antibodies) can be bound directly to a solid substrate where they are immobilized. These immobilized antibodies then capture protein present in the test sample. The THP thus immobilized is then bound by a labeling agent, such as a second THP antibody bearing a label. Alternatively, the second THP antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

b. Competitive Assay Formats.

In competitive assays, the amount of analyte (THP) present in the sample is measured indirectly by measuring the amount of an added (exogenous) analyte (THP) displaced (or competed away) from a capture agent (anti THP antibody) by the analyte present in the sample. In one competitive assay, a known amount of, in this case THP, is added to the sample and the sample is then contacted with a capture agent, in this case an antibody that specifically binds THP. The amount of THP bound to the antibody is inversely proportional to the concentration of THP present in the sample.

In a particularly preferred embodiment, the antibody is immobilized on a solid substrate. The amount of THP bound to the antibody may be determined either by measuring the amount of THP present in an THP/antibody complex, or alternatively by measuring the amount of remaining uncomplexed THP. The amount of THP may be detected by providing a labeled THP molecule.

A hapten inhibition assay is another preferred competitive assay. In this assay a known analyte, in this case THP, is immobilized on a solid substrate. A known amount of anti-THP antibody is added to the sample, and the sample is then contacted with the immobilized THP. In this case, the amount of anti-THP antibody bound to the immobilized THP is inversely proportional to the amount of THP present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Immunoassays in the competitive binding format can be used for crossreactivity determinations to permit one of skill to determine if a novel THP is sufficiently related to the claimed THP so as to fall under the claims of this invention. For example, a THP of SEQ ID NO:2 or SEQ ID NO:3 can be immobilized to a solid support. Proteins are added to the assay which compete with the binding of the antisera to the immobilized antigen. The ability of the proteins to compete with the binding of the antisera to the immobilized THP is compared to the binding by the same THP as was used to coat the solid support. The percent crossreactivity for the above proteins is calculated, using standard calculations. Those antisera with less than 10% crossreactivity with the THP of SEQ ID NO:2 or SEQ ID NO:3 are selected and pooled. The cross-reacting antibodies are optionally removed from the pooled antisera by immunoabsorption with the above proteins.

The immunoabsorbed and pooled antisera can be used in a competitive binding immunoassay, as described above, to analyze whether a second protein is an antifreeze protein of this invention. In the competitive binding immunoassay the protein, or immunogen, used to develop the antiserum competes with a second, uncharacterized protein or peptide in an antibody binding reaction. The two proteins are each assayed at a wide range of concentrations and the amount of each protein required to inhibit 50% of the binding of the antisera to the immobilized protein is determined. If the amount of the second protein required is less than 10 times the amount of the characterized immunogen (for example, SEQ ID NO:2, SEQ ID NO:3 or an immunogenic fragment thereof) that is required, then the second protein is said to specifically bind to an antibody generated to that characterized (antifreeze protein) immunogen.

c. Other Assay Formats.

Western blot (immunoblot) analysis can be used to detect and quantify the presence of antifreeze protein in a sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind THP. The anti-antifreeze protein antibodies specifically bind to THP on the solid support. These antibodies may be directly labeled or alternatively may be subsequently detected using labeled antibodies (e.g., labeled sheep anti-mouse antibodies) that specifically bind to the anti-antifreeze protein.

In addition to using nucleic acid probes for identifying novel forms of the class of proteins claimed herein, it is possible to use antibodies to probe expression libraries. This is a well known technology. (See Young & Davis, *Proc. Nat'l Acad. Sci. USA* 80:1194 (1982).) In general, a cDNA expression library may be prepared from commercially available kits or using readily available components. Phage vectors are preferred, but a variety of other vectors are available for the expression of protein. Such vectors include but are not limited to yeast, animal cells and *Xenopus oocytes*. One selects mRNA from a source that is enriched with the target protein and creates cDNA which is then ligated into a vector and transformed into the library host cells for immunoscreening. Screening involves binding and visualization of antibodies bound to specific proteins on cells or immobilized on a solid support such as nitrocellulose or nylon membranes. Positive clones are selected for purification to homogeneity and the isolated cDNA then prepared for expression in the desired host cells. A good general review of this technology can be found in METHODS OF CELL BIOLOGY, VOL. 37 entitled Antibodies in Cell Biology, Assai (ed.) 1993.

Where the antibodies are generated to a short peptide the test (uncharacterized) proteins are optionally denatured to fully test for selective binding, and it may be best to measure the test proteins against proteins of similar size, e.g., one would test a full length THP against a prototype full length THP even though the antisera was generated against a fragment of the prototype THP. This simplifies the test and avoids having to take into account conformational problems and molecular weight/molar concentrations in the determination of the results from the competitive immunoassays.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:34 (1986)).

B. Purification of THP

The polypeptides of this invention may be purified to substantial purity by standard techniques, from a variety of sources such as larval homogenates, tissue culture media, transgenic plants and animals, yeasts and bacteria. For standard purification procedures, including selective precipitation with such substances as ammonium sulfate; column chromatography, immunopurification methods, and others see, for instance, R. Scopes, PROTEIN PURIFICATION: PRINCIPLES AND PRACTICE, Springer-Verlag: New York (1982), U.S. Pat. No. 4,673,641, Ausubel, and Sambrook, all incorporated herein by reference.

1. Purification of THP from Bacterial Cultures

In the case of secreted proteins, the protein of interest can be isolated and purified from the broth in which bacteria have been grown without having to resort to the cell lysis methods detailed below.

2. Purification of THP from Bacterial Periplasm

It is anticipated that antifreeze protein expression from *E. coli* may be low and the protein is exported into the periplasm of the bacteria. The periplasmic fraction of the bacteria can be isolated by cold osmotic shock in addition to other methods known to skill in the art (see Ausubel and Trayer, H. R. and Buckley, III, C. E., *J. Biol. Chem.* 245(18):4842 (1970)).

To isolate proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The proteins present in the supernatant can be separated from the host proteins by standard separation techniques well known to those of skill in the art.

3. Purification of Inclusion Bodies

When recombinant proteins are expressed by the transformed bacteria in large amounts, typically after promoter induction; but expression can be constitutive, the proteins may form insoluble aggregates.

Purification of aggregate proteins (hereinafter referred to as inclusion bodies) involves the extraction, separation and/or purification of inclusion bodies by disruption of bacterial cells, typically but not limited by, incubation in a buffer of about 100–150 µg/mL lysozyme and 0.1% NONIDET P40®, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel and Sambrook and will be apparent to those of skill in the art.

The cell suspension is centrifuged and the pellet containing the inclusion bodies resuspended in buffer, e.g., 20 mM Tris-HCl (pH 7.2), 1 mM EDTA, 150 mM NaCl and 2% TRITON-X 100®, a non-ionic detergent. It may be necessary to repeat the wash step to remove as much cellular debris as possible. The remaining pellet of inclusion bodies may be resuspended in an appropriate buffer (e.g. 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties) together with a reducing agent such as DTT. The proteins that formed the inclusion bodies can then be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein.

After solubilization, the protein can be separated from other bacterial proteins by standard separation techniques.

4. Standard Protein Separation Techniques a. Solubility Fractionation

Often as an initial step and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20–30%. This will precipitate the most hydrophobic of proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

b. Size Differential Filtration

If the size of the protein of interest is known or can be estimated from the cDNA sequence, proteins of greater and lesser size can be removed by ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

c. Column Chromatography

Proteins can be separated on the basis of their size, net surface charge, hydrophobicity and affinity for ligands. In addition, antibodies raised against proteins can be conjugated to column matrices and the proteins immunopurified. All of these methods are well known in the art. See Scopes, R. K., Protein Purification: Principles and Practice, 2nd ed., Springer Verlag, (1987).

It will be apparent to one of skill that chromatographic techniques can be performed at any scale and using equipment from many different manufacturers (e.g., Pharmacia Biotech).

In a preferred embodiment, the purification of antifreeze protein from *E. coli* supernatant is accomplished by gel filtration and protein concentrations are determined according to Bradford, *Anal. Biochem.* 72:248–257 (1976).

d. Amino Acid Sequence

The amino acid sequences of the THP of this invention can be determined by, for example, Edman degradation, a technique which is well known in the art.

In addition to the internal sequencing, N-terminal sequencing can be performed by techniques known in the art.

e. Molecular Weight/Isoelectric Point

The molecular weight of a protein can be determined by many different methods, all known to one of skill in the art. Some methods of determination include: SDS gel electrophoresis, native gel electrophoresis, molecular exclusion chromatography, zonal centrifugation, mass spectroscopy, and calculation from sequencing. Disparity between results of different techniques could be due factors inherent in the technique. For example, native gel electrophoresis, molecular exclusion chromatography and zonal centrifugation depend on the size of the protein. The proteins of this invention are cysteine rich and might be expected to form many disulfide bonds, both intra and intermolecular. SDS gel electrophoresis depends on the binding of SDS to amino acids present in the protein. Some amino acids bind SDS more tightly than others, therefore, proteins will migrate differently depending on their amino acid composition. Mass spectroscopy and calculated molecular weight from the sequence utilize the frequency of amino acids present in the protein and multiply that frequency by the molecular weight of the amino acid. If the protein is glycosylated, mass spectroscopy will reflect this but calculated molecular weight will not.

In the present invention, the apparent molecular weight of THP isoforms using molecular exclusion chromatography was estimated to be between about 5 and 20 kD; by SDS gel electrophoresis, between about 6 kD to 14 kD. This agreed with the results obtained when molecular weights were calculated from the amino acid sequencing. However, THP species or isoforms within the scope of the invention are not limited to this MW range.

The isoelectric point of a protein can be determined by native gel (or disc) electrophoresis, isoelectric focussing or in a preferred method, by calculation given the amino acid content of the protein. The isoelectric point (pI) of two THP isoforms of the instant invention have been calculated to be about 6 to 9. However, THP species or isoforms within the scope of the invention are not necessarily limited to this range of isoelectric points.

f. Functional Assays

The THP species and isoforms of the invention can be identified and characterized by at least two functional properties, for example, thermal hysteresis and unique formation of ice crystals:

(1) Thermal Hysteresis

The THP proteins of this invention are approximately 10 to 50 fold more active than known fish (AFP) antifreeze proteins in a thermal hysteresis assay. Thermal hysteresis is defined as the difference between the solution freezing and melting temperatures. Freezing point is taken as the temperature at which uncontrollable crystal growth or spicular ice growth grows. Melting point is taken as the warmest temperature at which an ice crystal can be stably held without melting. TH activity can be measured in a nanoliter osmometer (Clifton Technical Physics, Martford, N.Y.) by methods well known in the art (see, for example. Chakrabartty & Hew, *Eur. J. Biochem.* 202:1057 (1991)). The starting ice crystal is usually 20 to 50 $\mu$m in diameter. The buffer used is typically 100 mM $NH_4HCO_3$ (pH 7.9) but other buffers of similar osmolarity can be used. Alternatively, TH activity can be measured in bacterial broth, tissue culture fluid, or hemolymph. However, the TH values obtained will depend on the osmolarity of the solution being measured.

The osmometer is a thermal electric cooling module with a separate but linked variable temperature control. This apparatus allow temperature regulation in the 0° C. to −9° C. range with a deep freeze mode to −40° C. The cooling module can be set up on a microscope stage where the growth and melt behavior of an ice crystal can be observed directly. The sample holder can be a small plate with dimensions of about 7 mm×7 mm×0.75 mm containing multiple small sample holes (about 0.35 mm in diameter). A drop of immersion oil, such as Cargille's B immersion oil, can be placed on the underside of the sample holder so that the sample holes are filled. 1 to 5 nL samples are then delivered into the center of the oil-filled hole by a capillary tube.

To measure TH activity, the samples are first frozen by cooling the samples rapidly to −40° C. and then allowing them to warm up to the melting point temperature. Once the melting point is reached, the samples are cooled by approximately 0.02° C. (10 milli-osmoles or mosmoles) per 10 to 15 seconds until the freezing temperature is reached. The conversion from the unit "osmos" to "° C." is 1.00 osmoles equals 1.86° C. In most instances, when the freezing point of a THP sample is reached, the ice crystal within the sample will grow spontaneously and rapidly. This leads to freezing of the entire sample.

Alternatively, a small ice crystal can be frozen onto the surface of a solution and the temperature of the solution immediately reduced to below freezing. The temperature below freezing when the nucleated ice crystal begins to grow is the freezing point depression or the thermal hysteresis measurement (see, Patterson & Duman, *J. Exp. Zool.* 210:361 (1979); and Wu, et al., *J. Comp. Physiol.* B 161:271 (1991). The thermal hysteresis activity of a solution is dependent on the concentration of the antifreeze protein, with the greater the concentration of the protein, the greater the activity shown by the solution. However, increased concentrations of THPs produce incrementally smaller increases in TH activity and a maximum is approached. In other words, the relationship between THP concentration and TH is hyperbolic, not linear.

The proteins of the present invention preferably have thermal hysteresis values greater than about 1.5° C. at about 1 mg/mL, more preferably greater than 2° C. at about 1 mg/mL and most preferably between about 1.5° C. to 3.0° C. at about 1 mg/mL.

(2) Unique Formation of Ice Crystals

In addition to having approximately 10 to 50 fold more specific activity than previously known fish antifreeze proteins, the proteins of this invention produce different shaped ice crystals. Under microscopic analysis, fish antifreeze proteins produce ice crystals which are hexagonal bipyramids with flat, well-defined facets. The THP of this invention, on the other hand, form rounded crystals with no obvious expression of facets.

IV. USE OF ANTIFREEZE PROTEINS AND RELATED GENES

The proteins or genes encoding the THP may be used in ways to suppress ice crystal growth. For a comprehensive review of uses of antifreeze proteins, see U.S. Pat. No. 5,118,792. The THP of this invention may be introduced in the protein form, or they may be introduced as genes which are expressed endogenously at a level which should be attainable by expressing an antifreeze protein in a cell under the control of a suitable strong promoter to produce the proteins. Suitable concentrations of THP will vary depending on the use, but will typically be in the range of from about one part per billion to about one part per thousand (i.e., 1 μg/L to 1 μg/L).

In one embodiment of the invention, the proteins will be introduced to foodstuffs. This has a number of different aspects. One is the introduction into plant foodstuffs, either into the entire plant and thus conferring some degree of general resistance to damage from subfreezing climatic conditions, or into a plant part such as the fruit or vegetable portion to minimize damage specifically to those particular plant organs upon freezing. Exemplary plant parts are stems, roots, leaves, flowers, petioles, pericarp, seeds, vegetative tissue, tubers and so forth.

The texture, taste, and useful storage life of frozen vegetables will be improved, for example, celery, potatoes, asparagus, peas, carrots, beans, broccoli, sweet corn and spinach. Similarly, the texture, taste and useful storage life of fruits will be enhanced, including strawberries, blueberries, raspberries, citrus fruits, bananas, grapes, kiwis, peaches, pineapples, plums, cherries, tomatoes and mangoes.

This introduction into plant and other products may be most easily accomplished by genetic introduction of appropriate nucleic acids into the target organism. Expression of the nucleic acid, either constitutively or inducibly, before food processing has begun, or after harvesting and processing has begun, may lead to sufficiently high levels of the polypeptide to effectively protect the foodstuff, such as up to 0.5%, but more preferably up to about 0.1% of total plant protein by mass. Expression can also be on a tissue specific basis. For example, linkage to ripening genes in fruits may result in expression even after harvesting from the producing plant.

The polypeptides may also be added into foods which are expected to be frozen. Many frozen foods are intended to be consumed in the cold state, for example, ice cream, frozen yogurt, ice milk, sherbet, popsicles, frozen whipped cream, frozen cream pies, frozen puddings and the like. In particular, texture and flavor are adversely affected by the formation of large ice crystals throughout a freeze-thaw cycle that occurs in most home frost-free freezers or upon sustained storage in the frozen state. This ice crystal growth process may be prevented entirely, or at least minimized by the addition of antifreeze polypeptides. The purified antifreeze protein may be either incorporated throughout the foodstuff, or may, alternatively, be applied to the surface where condensation and crystal formation is expected to occur most readily.

In another embodiment, the genes that encode the THP of this invention are used to transform microorganisms which when added to foodstuffs, protect the foodstuffs or the microorganism from freezing. For example, bacteria such as *Streptococcus thermophilus* and *Lactobacillus bulgaricus* can be added to dairy products that is intended to be sold as frozen yogurt. In addition to fermenting the dairy products to produce yogurt, the THP expressed by the bacteria will protect the product from home freezer freeze-thaw cycles and produce a more palatable product.

Another use would be to transform dough yeast with nucleic acids encoding THP. Upon incorporation and expression of this gene into the yeast, and use of these yeast in frozen dough, the dough will naturally leaven upon thawing because the yeast viability will remain high upon thawing. Because less damage accumulates from storage in the presence of these antifreeze polypeptides and thawed samples preserve high viability, either longer storage times will be possible, or perhaps much smaller aliquots will need to be stored.

There are various embodiments not specific to the food freezer. One is the use of THP to protect plants from climatic freezing conditions. The THP may be either internally incorporated into the cytoplasm by expression of an introduced gene, or the proteins may be externally applied to the plants. External application may be achieved either by direct application of the proteins to the plant, or by the external deposit onto the plant of an organism which secretes the proteins. These same alternatives for introduction apply to other uses as well.

In addition to plants, it is envisioned that the THP of this invention can be used to produce transgenic fish that can withstand sub-zero temperatures. While some polar fish do synthesize antifreeze proteins, most fish do not live in environments where the water temperature drops below 0°

C. However, transgenic fish containing exogenous nucleic acid encoding THP could be held and perhaps partially raised in sub-zero salt-water. In particular, salt-water fish being raised in farms, most particularly salmon.

In addition to the above embodiments, it is envisioned that the THP of this invention can be used to regulate the expression of endogenous THP genes within a cold-tolerant organism. The expression of antifreeze protein gene produces may be increased as a method of preparing, e.g., for subsequent isolation, endogenous antifreeze proteins. Conversely, by downregulating endogenous antifreeze gene expression, an otherwise cold-tolerant pest may be converted to a less aggravating phenotype.

Methods of altering the expression of endogenous genes are well known to those of skill in the art. Typically such methods involve altering or replacing all or a portion of the regulatory sequences controlling expression of the particular gene that is to be regulated. In a preferred embodiment, the regulatory sequences (e.g., the native promoter) upstream of one or more of the THP are altered.

This is typically accomplished by the use of homologous recombination to introduce a heterologous nucleic acid into the native regulatory sequences. To downregulate expression of one or more THP gene products, simple mutations that either alter the reading frame or disrupt the promoter are suitable. To upregulate expression of the THP gene products, the native promoter(s) can be substituted with heterologous promoter(s) that induce higher than normal levels of transcription.

In a particularly preferred embodiment, nucleic acid sequences comprising the structural gene in question or upstream sequences are utilized for targeting heterologous recombination constructs. Utilizing the structural gene sequence information provided in SEQ ID NO:1, one of skill in the art can create homologous recombination constructs with only routine experimentation.

The use of homologous recombination to alter expression of endogenous genes is described in detail in U.S. Pat. No. 5,272,071, WO 91/09955, WO 93/09222, WO 96/29411, WO 95/31560, and WO 91/12650. Homologous recombination in mycobacteria is described by Azad, et at., *Proc. Nat'l Acad. Sci. USA* 93:4787 (1996); Baulard, et al., *J. Bacteriol.* 178:3091 (1996); and Pelicic, et al., *Mol. Microbiol.* 20:919 (1996). Homologous recombination in animals has been described by Moynahan, et al., in *Hum. Mol. Genet.* 5(7):875 (1996) and in plants by Offringa, et al., *EMBO J.* 9(10):3077 (1990).

Another embodiment is the introduction of an antifreeze protein into aqueous liquids surrounding an organ, tissue or other biological sample. One particular use would be during transportation to a hospital for a transplantation operation or for storage purposes. The antifreeze protein should allow short- or long-term storage at a subfreezing temperature, thereby minimizing inherent metabolism or degradation, but with substantially diminished cellular damage from ice crystal growth. Other medically important temperature sensitive biological samples are blood and blood products, therapeutic agents, protein drugs, bioassay reagents and vaccines.

Yet another embodiment is the introduction of an antifreeze protein into cells or their extracts destined for frozen storage. For example, bacterial cells, yeast cells, plant cells and, most particularly, animal cells containing the THP have increased cell or tissue viability with minimal or no loss of inherent characteristics due to the freeze-thaw process. Sub-cellular samples or cellular extracts may have similar sensitivities to freezing, especially on prolonged storage. Typical examples will be in vitro protein translation systems, enzyme preparations, and particularly samples which contain sensitive membrane components, such as chloroplast or mitochondrial membrane preparations. In particular, samples containing organelles may display increased resistance to freezing damage upon addition of these antifreeze polypeptides. Soft animal tissues will exhibit less damage upon freezing in the presence of the subject polypeptides, and addition of the polypeptides will be useful in situations when cellular integrity upon freezing and subsequent thawing is important or desired, such as for tissue culture deposits. Thus, samples destined for frozen storage, such as for cell or tissue depositories, might routinely have the proteins added to them. Among the cell types often stored are genetic variants of bacteria, fungi (including yeast), and, particularly, higher eukaryote cells (such as hybridoma strains and tissue culture cell lines).

Also included in the invention are compositions and uses based on the mixture of THP with stabilizers well known to those skilled in the art and other additives. These compounds may be present to inhibit decay, inhibit oxidation, prevent discoloration, inhibit microbial growth, stabilize emulsions and so forth.

Also included in the invention are compositions based on THPs suitable for depressing the freezing point or inhibiting freezing in non-organic systems, such as for use in deicing treatments.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

Example 1

THP from Choristoneura sp. Larvae

The following example details the isolation of THP from the hemolymph of the lepidopteran species, *Choristoneura fumiferana*, which is known to winter farther north than many other species in that order. Homogenates of two species in the Choristoneura genus, namely *Choristoneura fumiferana* and *Choristoneura occidentalis*, had displayed particularly high antifreeze activity (method of quantitation described below) in the laboratory.

Eastern spruce budworm (*C. fumiferana*) second instar larvae were purchased from the Insect Production Unit of the Forest Pest Management Institute, Forestry Canada, Sault Ste. Marie, Ontario, Canada. After 20 to 30 weeks at 2 to 4° C., diapausing larvae were collected from cheese-cloth and used as described below.

Antifreeze activity was assayed during extraction and purification of THP by thermal hysteresis (i.e., the difference in temperature (°C.) between the freezing and melting points of a solution) using a Clifton Direct Reading Nanoliter Osmometer (Clifton Technical Physics, Hartford, N.Y.) according to the method of Chakrabartty et al. (1991). During these assays the effects of the AFP on ice crystal morphology were monitored and recorded by video microscopy. Total protein concentration was monitored by colorimetric assays (Bradford, 1976) or by absorbance at 230 nm ($A_{230}$).

Maintaining all solutions and samples on ice, 100 mg of second instar larvae of eastern spruce budworm were homogenized in 250 µL 0.1 M NH$_4$HCO$_3$, pH 8.0, containing 1 mM phenylmethylsulfonyl fluoride (PMSF, a protease inhibitor) and 0.5 mM phenylthiourea (a phenyl oxidase inhibitor). The homogenate was centrifuged in a microfuge at 10,000×g for 2 min at 4° C., and subsequently dialyzed overnight against the homogenization buffer. The dialysate was loaded onto a filter spin column (Bio-Rad, Hercules, Calif.) to remove cellular debris and particulate matter.

THPs were purified from the resulting filtrate using chromatographic procedures that are standard for the isolation of fish AFPs from serum (Fourney et al., 1984; Li et al., 1985; Ng et al., 1986). First, the THPs were size-selected by gel filtration at 4° C. on a Sephadex G-75 column (Pharmacia, Uppsala, Sweden) in the homogenization buffer. The THPs eluted just after the void peak. The fractions with highest thermal hysteresis activity were then pooled, lyophilized, suspended in 1 mL H$_2$O, relyophilized and resuspended in 100 µL H$_2$O. The sample was next subjected to high performance liquid chromatography (HPLC) (Beckman) on a C18 reversed-phase column in 0.1% trifluoroacetic acid (TFA) using a linear acetonitrile gradient varying from 0 to 65% (v/v). As shown in FIG. 1, THPs eluted from this column as a cluster of peaks, labelled 22, 23 and 24, which demonstrated thermal hysteresis activity. This was consistent with the fractionation of a set of THP isoforms.

In certain trials, the isoforms were refractionated by HPLC to improve their purity. This procedure gives a single molecular weight protein product for each isoform as determined by MALDI (matrix-assisted laser desorption/ionization) mass spectrometry. Electrospray mass spectrometry on a Finnigan TSQ700 triple quadrupole mass spectrometer (Finnigan, San Jose, Calif.) was used to identify at least 3 individual AFP isoforms, all having molecular weights of approximately 9,000 Da. The THP isoforms were also subjected to amino acid analysis (Model 920A, Applied Biosystems, Inc., Foster City, Calif.).

Example 2

Protein Sequencing of THP

2 µg of the THP isoform corresponding to peak 24 of FIG. 1 were reduced and alkylated on cysteines by reaction with iodoacetamide. The covalently modified THP was digested to completion with trypsin and the digestion products were resolved by reversed-phase HPLC on a Vydac C18 column in 0.1% trifluoroacetic acid. The elution profile was monitored at three wavelengths: 210 nm, 277 nm and 292 nm. A few individual, well-separated tryptic peptides were analyzed by MALDI mass spectrometry performed on a Finnigan Lasermat mass spectrometer (Finnigan, San Jose, Calif.). Three such peptides were sequenced by automated Edman degradation (Harvard Microchem, Harvard University) using an Applied Biosystems, Inc. Model 477A protein sequencer with Model 120A phenylthiohydantoin (PTH)-amino acid analyzer. The peptide sequences obtained are shown as SEQ ID NO:6, SEQ ID NO:7 and SEQ ID NO:8. In addition, the N-terminal sequence of this isoform was determined from sequencing of the undigested protein and is shown as SEQ ID NO:9. A hyphen signifies an amino acid residue that cannot be conclusively identified using the protocol described; however, in the vast majority of cases, such a residue will be a cysteine. The inventors recognized that SEQ ID NO:9 shows an overlap with one of the internal tryptic peptide sequences, namely SEQ ID NO:7.

The N-terminal sequence of the isoform corresponding to fraction 23 of FIG. 1 was determined and is shown as SEQ ID NO:10. Although the sequence obtained does not extend far enough to show any overlap with SEQ ID NO:7, the inventors recognized that it is clearly homologous to the N-terminal sequence shown as SEQ ID NO:9. This confirmed the isoform status of neighboring HPLC peaks.

Example 3

Cloning and Sequencing THP cDNAs

The nucleic acid sequence (SEQ ID NO:1) and protein sequence information (SEQ ID NO:2 and SEQ ID NO:3) can be used to design PCR primers and oligonucleotides for the identification of spruce budworm antifreeze gene(s) and cDNA. PCR primers pairs that are known to generate THP sequences, such as SEQ ID NO:4 and SEQ ID NO:5, and, SEQ ID NO:13 and SEQ ID NO:14, can be used to directly amplify new THP species and isoforms.

Alternatively, oligonucleotides can be useful to detect THP-encoding nucleic acid using a variety of hybridization techniques and conditions. These oligonucleotides can be generated using any known technique, including PCR, enzymatic restriction digestion of isolated DNA or organic synthesis. These nucleic acids can be labeled for detection and hybridized to DNA by any known technique, as described above.

Total RNA can be extracted from Choristoneura sp. larvae and enriched for mRNA using the QuickPrep Micro mRNA Purification Kit (Pharmacia, Piscataway, N.J.) according to the manufacturer's instructions. The mRNA is then used to make cDNA templates by reverse transcription using, for example, the avian myeloblastosis virus (AMV) reverse transcriptase (Pharmacia) as described by Sambrook.

PCR can be performed on the cDNA using, for example, a Techne PHC-3 thermal cycler (Techne, Princeton, N.J.) using any set of primers whose sequence is based on a known THP sequence, such as SEQ ID NO:1, or pairs of primers that are known to amplify THP sequences, such as SEQ ID NO:4 and SEQ ID NO:5, and, SEQ ID NO:13 and SEQ ID NO:14.

The amplification can involve a variety of annealing conditions, for example, annealing for 40 sec at 52° C., followed by extension for 15 sec at 72° C. and then denaturation for 1 min at 94° C. This is repeated for a total of about 30 to 40 cycles, yielding a DNA product, which is purified. The PCR product can be sequenced by any known technique, such as the dideoxy-chain termination method using a Dye Terminator Cycle Sequencing Kit™ Ready Reaction Kit (Applied Biosystems, Foster City, Calif.) and a Model 373A DNA Sequencer (Applied Biosystems). The PCR product, once identified as a THP sequence, can be further labeled and used as a hybridization probe, as described above.

Computer databases and programs can be used to analyze the resultant DNA sequence for its sequence identity, or homology, to known THP sequences. For example, PC/Gene™ software (IntelliGenetics Inc., Mountain View, Calif.) aligns sequences and displays open reading frames. BLAST N and BLAST D search algorithms can be employed to search the GenBank database (NIH, Bethesda, Md.) for any matches between the derived THP sequence and known sequences in the database.

Example 4

Raising of Antibodies Directed to THPs

A hydrophilic peptide of the 9,060 Da mature THP (SEQ ID NO:3) was identified by the inventors as a good candidate for an antigenic determinant against which useful antibodies could be raised. This peptide has the amino acid sequence of SEQ ID NO:12. The peptide, having an acetylated N-terminus and an amidated C-terminus as shown, was chemically synthesized by standard techniques. Polyclonal antibodies against this peptide were raised in New Zealand white rabbit at the Core Facility, Queen's University, Kingston, ON, Canada, using procedures outlined generally in Harlow and Lane (1988). This antiserum has been used to detect THP in western blots, and can be used to screen a recombinant expression library for THP, as described above.

Example 5

Effects of THP on Ice Crystal Formation

Figure 3A:
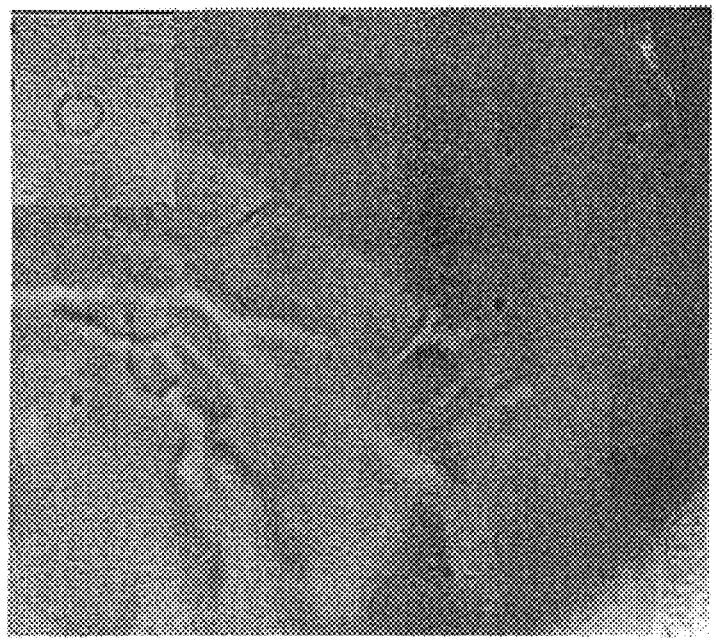
FIG. 3A is a photomicrograph of ice formed from a crude extract of second instar larvae of spruce budworm.
Figure 3B:
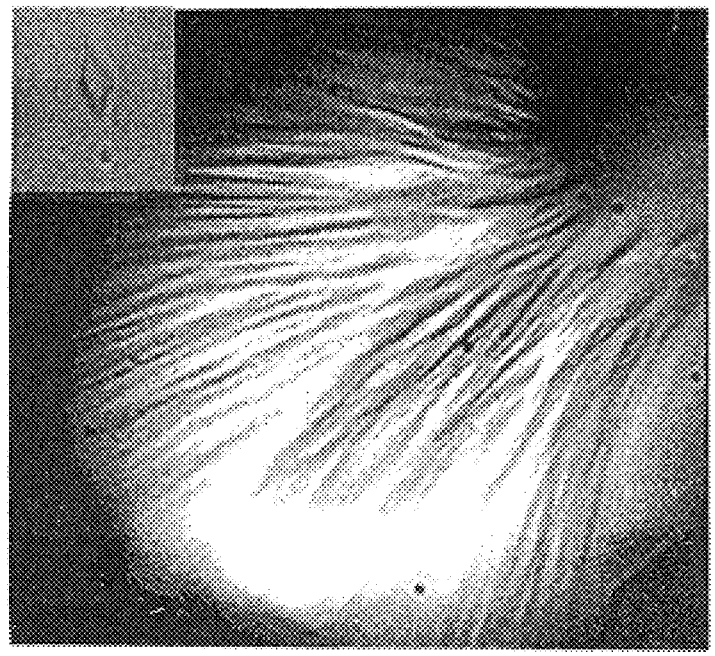
FIG. 3B is a photomicrograph of ice formed from a solution containing about 5 mg/ml of Type III THP protein (in fish, THP protein is also known as AFP protein) from ocean pout.

As described in Example 1, thermal hysteresis assays of THPs were recorded by video microscopy. This led to the following interesting observation: When a solution containing the THP of the invention does freeze, the ice forms smooth waves or fronts. This is shown in FIG. 3A, a photomicrograph of ice formed from a crude extract of second instar larvae of spruce budworm. In contrast, when a solution containing a fish THP freezes, the ice is typically sharp and spicular. An example of this, ocean pout Type III antifreeze protein (5 mg/mL), is shown in FIG. 3B. Such sharp ice formations could cause shearing of cells.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An isolated or recombinantly expressed antifreeze protein, said protein comprising the following properties:
   (i) an apparent molecular weight of between about 5 and 20 kDa as determined by molecular exclusion chromatography;
   (ii) a thermal hysteresis activity of greater than about 1.5° C. at a concentration of about 1 mg/mL; and
   (iii) (a) specific binding to an antibody raised against an antifreeze protein selected from the group consisting of SEQ ID NO:2 and SEQ ID NO:3; and,
   (b) encoded by a nucleic acid which specifically hybridizes to a nucleic acid comprising a sequence as set forth in SEQ ID NO:1 under stringent conditions, wherein the stringent conditions include a wash step comprising a wash in 0.2×SSC at a temperature of about 65° C. for about 15 minutes.

2. The isolated or recombinant antifreeze protein of claim 1, wherein the antifreeze protein is synthesized by an insect cell, a mammalian cell, a yeast cell, a plant cell or a bacterial cell.

3. The isolated or recombinant antifreeze protein of claim 1, wherein the nucleic acid encoding the antifreeze protein is isolated from Choristoneura sp.

4. The isolated or recombinant antifreeze protein of claim 1, wherein the thermal hysteresis activity is greater than about 2° C. at a concentration of about 1 mg/mL.

5. The isolated or recombinant antifreeze protein of claim 1, wherein the protein comprises a sequence selected from the group consisting of SEQ ID NO:2 and SEQ ID NO:3.

6. The isolated or recombinant antifreeze protein of claim 1, wherein the protein is expressed by a baculoviris vector.

7. The isolated or recombinant antifreeze protein of claim 1, where in the antifreeze protein is synthesized by a mammalian cell.

8. A method for decreasing the freezing point of an aqueous solution, said method comprising the addition of the antifreeze protein of claim 1 to said aqueous solution.

9. The method of claim 8, wherein the antifreeze protein is encoded by a nucleic acid comprising a sequence as set forth in SEQ ID NO:1.

10. The method of claim 8, wherein the antifreeze protein is produced by recombinant means in a mammalian cell, a bacterial cell, a yeast cell, an insect cell or a plant cell.

11. The method of claim 8, wherein the antifreeze protein comprises a sequence as set forth in SEQ ID NO:2 or SEQ ID NO:3.

12. The method of claim 8 or claim 9, wherein the concentration of antifreeze protein in the aqueous solution is between about one part per billion (1 μg/L) to about one part per thousand (1 g/L).

13. A liquid comprising a recombinant antifreeze protein comprising the following properties:
  (i) an apparent molecular weight of between about 5 and 20 kDa as determined by molecular exclusion chromatography;
  (ii) a thermal hysteresis activity of greater than about 1.5° C. at a concentration of about 1 mg/mL; and
  (iii) (a) specific binding to an antibody raised against an antifreeze protein selected from the group consisting of SEQ ID NO:2 and SEQ ID NO:3; and,
  (b) encoded by a nucleic acid which specifically hybridizes to a nucleic acid comprising a sequence as set forth in SEQ ID NO:1 under stringent conditions, wherein the stringent conditions include a wash step comprising a wash in 0.2×SSC at a temperature of about 65° C. for about 15 minutes.

14. The liquid of claim 13, wherein the concentration of the antifreeze protein is between about one part per billion (1 μg/L) to about one part per thousand (1 g/L).

* * * * *